(12) United States Patent
Baell et al.

(10) Patent No.: US 6,355,683 B1
(45) Date of Patent: Mar. 12, 2002

(54) FC RECEPTOR MODULATORS AND USES THEREOF

(75) Inventors: Jonathan B. Baell, Ivanhoe; Thomas P. J. Garrett, Brunswick; P. Mark Hogarth, Williamstown; Barry R. Matthews, Olinda; Thomas D. McCarthy, East Malvern; Geoffrey A. Pietersz, Greensborough, all of (AU)

(73) Assignee: Ilexus Pty Limited, Victoria (AU)

( * ) Notice: Subject to any disclaimer, the term of this patent is extended or adjusted under 35 U.S.C. 154(b) by 0 days.

(21) Appl. No.: 09/393,598

(22) Filed: Sep. 10, 1999

Related U.S. Application Data

(60) Provisional application No. 60/099,855, filed on Sep. 11, 1998, provisional application No. 60/131,938, filed on Apr. 30, 1999, and provisional application No. 60/148,479, filed on Aug. 11, 1999.

(51) Int. Cl.⁷ .............................................. A61K 31/194
(52) U.S. Cl. ...................................................... 514/568
(58) Field of Search ................................. 514/568, 748

(56) References Cited

U.S. PATENT DOCUMENTS

| 4,686,282 A | 8/1987 | Hahn | ........................ 530/327 |
| 4,752,601 A | 6/1988 | Hahn | ........................... 514/14 |

FOREIGN PATENT DOCUMENTS

| WO | WO 86/01211 A | 2/1986 |
| WO | WO 97/40033 A | 10/1997 |
| WO | WO 99/40117 A | 8/1999 |

OTHER PUBLICATIONS

Tabata et al., Pharm. Res. (1993), 10(4), 487–96 (abstract).*
Chemical Abstracts CA:55:1138e (1955).*

* cited by examiner

*Primary Examiner*—Phyllis G. Spivack
(74) *Attorney, Agent, or Firm*—Sheridan Ross P.C.

(57) ABSTRACT

This invention relates to a pharmaceutical composition comprising a Fc receptor modulating compound and a pharmaceutically acceptable carrier. The present invention also relates to a method for treating a variety of diseases using a Fc receptor modulating compound.

50 Claims, 20 Drawing Sheets

BRI6727

BRI6728

BRI6734

BRI6813

BRI6795

BRI6796

BRI6797

BRI6798

BRI6799

BRI6800

BRI6801

BRI6802

BRIX114

BRI6803

BRI6814

BRI6815

BRI6816

BRI6817

BRI6822

BRI6823

BRI6824

BRI6825

BRI6829

BRI6855

BRI6856

BRI6857

BRI6864

BRI6865

BRI6868

BRI7001 R = NH$_2$
BRI7002 R = NH$_3$Cl

BRI7009

BRI7012

Serial dilutions of compounds at specified concentrations, prefix BRI and designated as indicated, were preincubated with receptor and injected over IgG and extent of receptor binding determined (shown as Response Units - Y axis).

Activation of platelets in the presence of agonist only.
Platelets (100 x10⁶/ml) were mixed in the presence of FcγRIIa agonist (HAGG, 200μg/ml) and PBS and the rate of platelet aggregation was measured as the gradient of the change to percent light transmission (x) over time (y).

FC RECEPTOR MODULATORS AND USES THEREOF

CROSS-REFERENCE TO RELATED APPLICATIONS

This application claims the benefits of U.S. Provisional Application No. 60/099,855, filed Sep. 11, 1998, U.S. Provisional Application No. 60/131,938, filed Apr. 30, 1999, and U.S. Provisional Application No. 60/148,479, filed Aug. 11, 1999.

FIELD OF THE INVENTION

The present invention relates to compounds which modulate binding of immunoglobulins to Fc receptors and uses thereof.

BACKGROUND OF THE INVENTION

Fc receptors (FcR) are a family of highly related receptors that are specific for the Fc portion of immunoglobulin (Ig). These receptors have major roles in normal immunity and resistance to infection and provide the humoral immune system with a cellular effector arm. Receptors have been defined for each of the immunoglobulin classes and as such are defined by the class of Ig of which they bind (i.e. Fc gamma receptor (FcγR) bind gamma immunoglobulin (IgG), Fc epsilon receptor (FcγR) bind epsilon immunoglobulin (IgE), Fc alpha receptor (FcαR) bind alpha immunoglobulin (IgA)). Among the FcγR receptors, three subfamily members have been defined; FcγRI, which is a high affinity receptor for IgG; FcγRII, which are low affinity receptors for IgG that avidly bind to aggregates of immune complexes; and FcγRIII, which are low affinity receptors that bind to immune complexes. These receptors are highly related structurally but perform different functions. The structure and function of FcγRII is of interest because of its interaction with immune complexes and its association with disease.

FcγR are expressed on most hematopoietic cells, and through the binding of IgG play a key role in homeostasis of the immune system and host protection against infection. FcγRII is a low affinity receptor for IgG that essentially binds only to IgG immune complexes and is expressed on a variety of cell types including, for example monocytes, macrophages, neutrophils, eosinophils, platelets and B lymphocytes. FcγRII is involved in various immune and inflammatory responses including antibody-dependent cell-mediated cytotoxicity, clearance of immune complexes, release of inflammatory mediators and regulation of antibody production. The binding of IgG to a FcγR can lead to disease indications that involve regulation by FcγR. For example, the autoimmune disease thrombocytopenia purpura involves tissue (platelet) damage resulting from FcγR-dependent IgG immune complex activation of platelets or their destruction by FcγR+ phagocytes. In addition, various inflammatory diseases are known to involve IgG immune complexes (e.g. rheumatoid arthritis, systemic lupus erythematosus), including type II and type III hypersensitivity reactions. Type II and type III hypersensitivity reactions are mediated by IgG, which can activate either complement-mediated or phagocytic effector mechanisms, leading to tissue damage.

Because FcR are involved in a variety of biological mechanisms, there is a need for compounds which affect the binding of immunoglobulins to FcR. There is also a need for using such compounds to treat a variety of illnesses.

SUMMARY OF THE INVENTION

The present invention provides a pharmaceutical composition comprising:
(a) a compound selected from the group consisting of an aromatic compound of the formula:

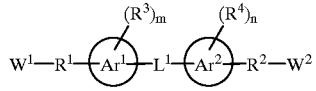

a heteroaromatic compound of the formula:

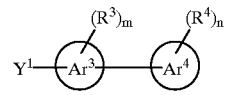

a cyclic compound of the formula:

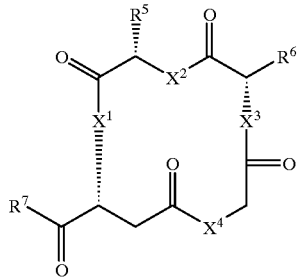

a bicyclic compound of the formula:

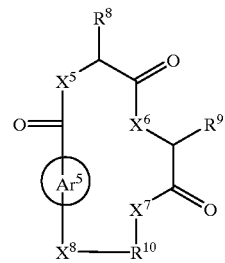

and an amino acid derivative of the formula:

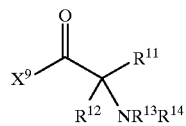

or salts thereof,
wherein
each of $W^1$ and $W^2$ is independently $CO_2R^{15}$, $C(=NH)NH(OH)$, $SO_3R^{15}$, $C(=NH)NH_2$, $OPO(OR^{15})_2$, $C(=O)$ $CF_3$ or $PO(OR^{15})_2$;
each of $Ar^1$, $Ar^2$, $Ar^4$ and $Ar^5$ is independently $C_6-C_{20}$ aryl or $C_1-C_{20}$ heteroaryl;
$Ar^3$ is $C_1-C_{20}$ heteroaryl;
each of $X^1$, $X^2$, $X^3$, $X^4$, $X^5$, $X^6$, $X^7$ and $X^8$ is independently methylene, O, S or $NR^{16}$;
each of $R^1$ and $R^2$ is independently a bond, $C_1-C_6$ alkylene, or halogenated $C_1-C_6$ alkylene;

each of $R^3$ and $R^4$ are independently halogen, $-Z^1$ or $C_1-C_6$ alkyl;

each of $X^9$, $Y^1$ and $Z^1$ is independently $OR^{17}$, $SR^{17}$ or $NR^7R^{18}$;

each of $R^5$ and $R^6$ is independently amino acid side chain residue or a moiety of the formula $-R^{19}-W^3$;

each of $R^8$, $R^9$ and $R^{11}$ is independently an amino acid side chain residue, provided $R^{11}$ is not H or $CH_3$;

$R^7$ is $OR^{20}$, $NR^{21}R^{22}$, or from about 1 to about 10 amino acids;

$R^{10}$ is $C_1-C_6$ alkylene;

$R^{12}$ is $C_1-C_6$ alkyl or $C_6-C_{20}$ aralkyl;

$W^3$ is $C(=O)X^{10}$;

$X^{10}$ is $OR^{23}$ or $NR^{24}R^{25}$;

each of $R^{13}$, $R^{15}$, $R^{17}$, $R^{18}$, $R^{20}$, $R^{21}$, $R^{23}$ and $R^{24}$ is independently hydrogen or $C_1-C_6$ alkyl;

each $R^{16}$ is independently H, $C_6-C_{20}$ aryl or an amide protecting group;

$R^{19}$ is $C_1-C_6$ alkylene;

each of $R^{22}$ and $R^{25}$ is independently H, $C_1-C_6$ alkyl or an amide protecting group;

$R_{14}$ is H, $C_1-C_6$ alkyl or an amine protecting group;

L is a linker comprising from 1 to about 20 atoms; and each of m and n is independently an integer from 0 to 2; and (b) a pharmaceutically acceptable carrier.

The present invention also provides a method for using a compound selected from the group consisting of substituted or unsubstituted benzoic acids; nucleosides and analogs thereof; folic acid and its derivatives; peptides comprising from about 2 to about 10 amino acid residues or derivatives thereof, preferably tripeptides or hexapeptides; macrocyclic compounds containing a ring moiety which comprises from about 8 atoms to about 18 atoms, preferably cyclic peptides or derivatives thereof; and compounds of the above formulas to modulate, e.g., inhibit or enhance, binding of immunoglobulins to Fc receptors in a patient. In a particular embodiment of the present invention, this modulation of Fc receptors by the above identified compounds is used to treat a disease where aggregates of antibodies are produced or where immune complexes are produced by contact of antibody with intrinsic or extrinsic antigen. Modulation of Fc receptors by the above identified compounds can also be used to reduce IgG-mediated tissue damage, to reduce IgE-mediated response and/or to reduce inflammation in a patient.

DETAILED DESCRIPTION OF THE INVENTION

Figure 1:
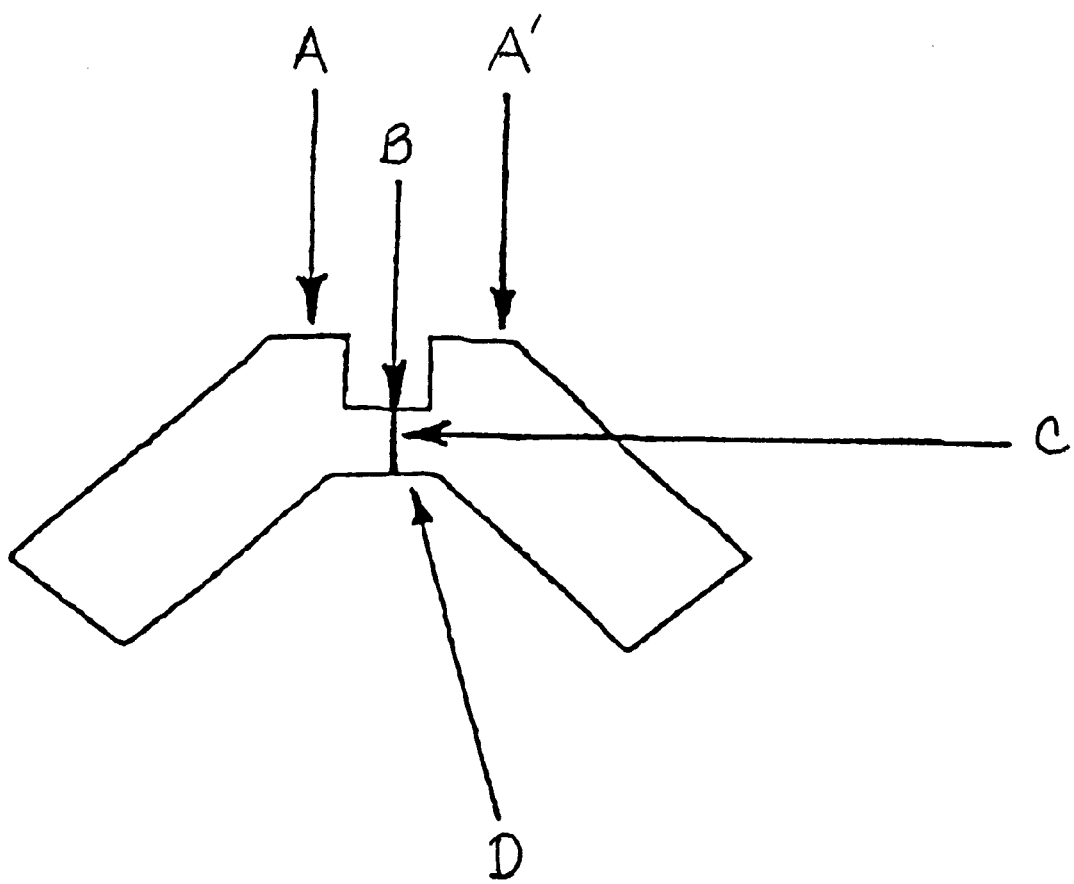
FIG. 1 is a schematic illustration of a binding site on FcγRIIa receptor.
Figure 2:
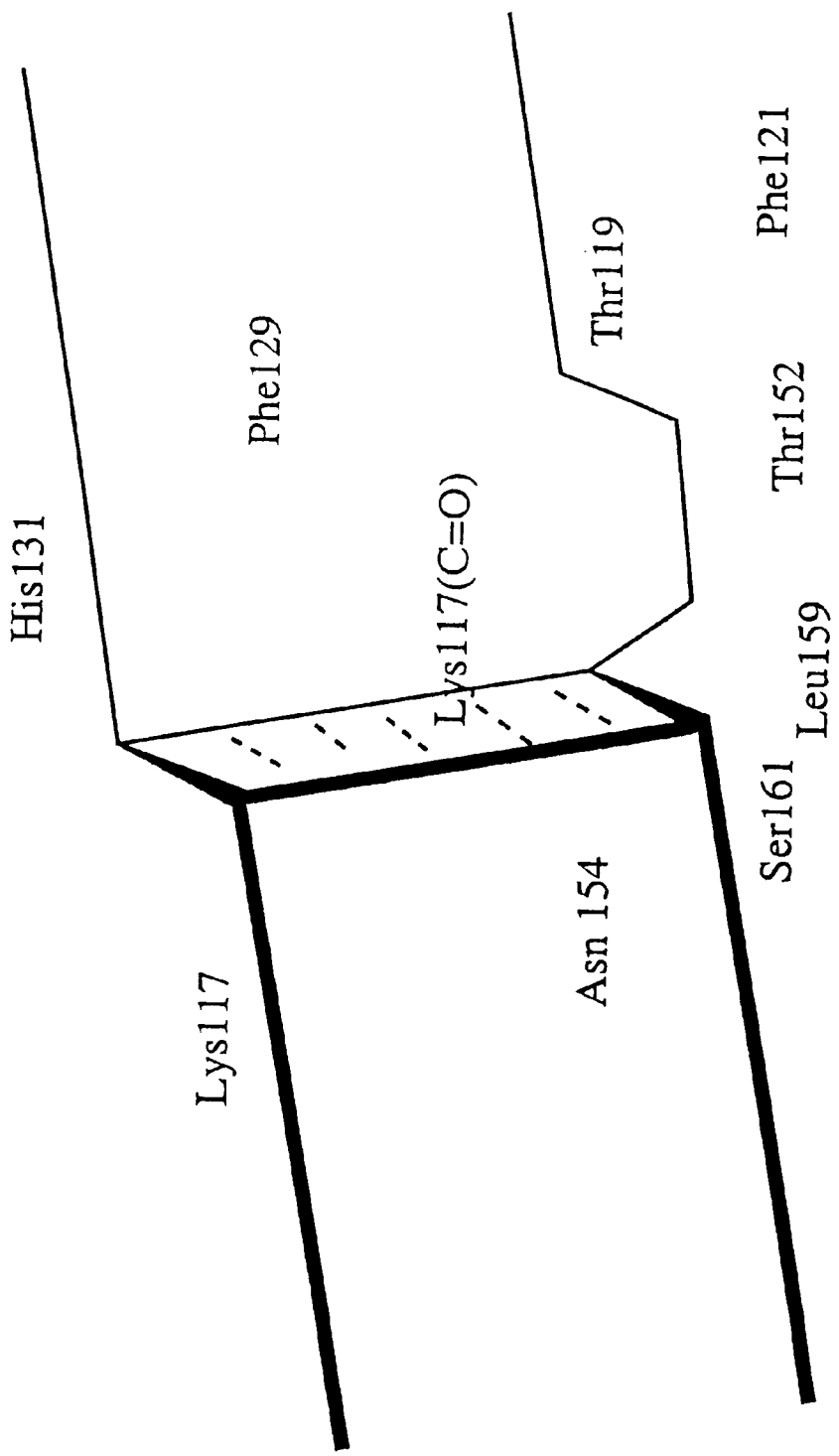
FIG. 2 shows a lateral schematic view of the groove, illustrating only one face, with the protein residues of interest.
Figure 3:
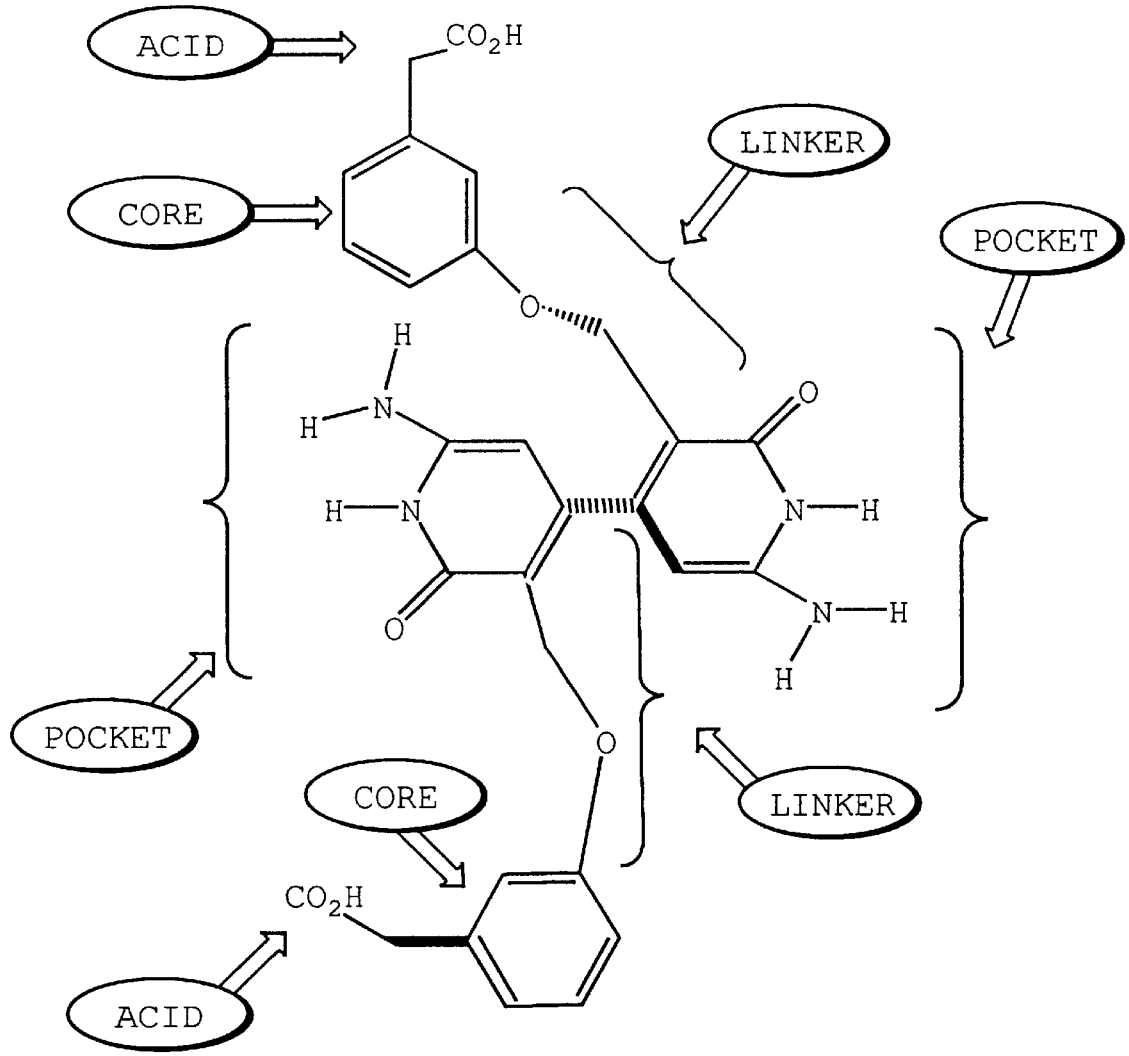
FIG. 3 illustrates how a particular ligand relates to the general design of a compound of the present invention.
Figure 4:
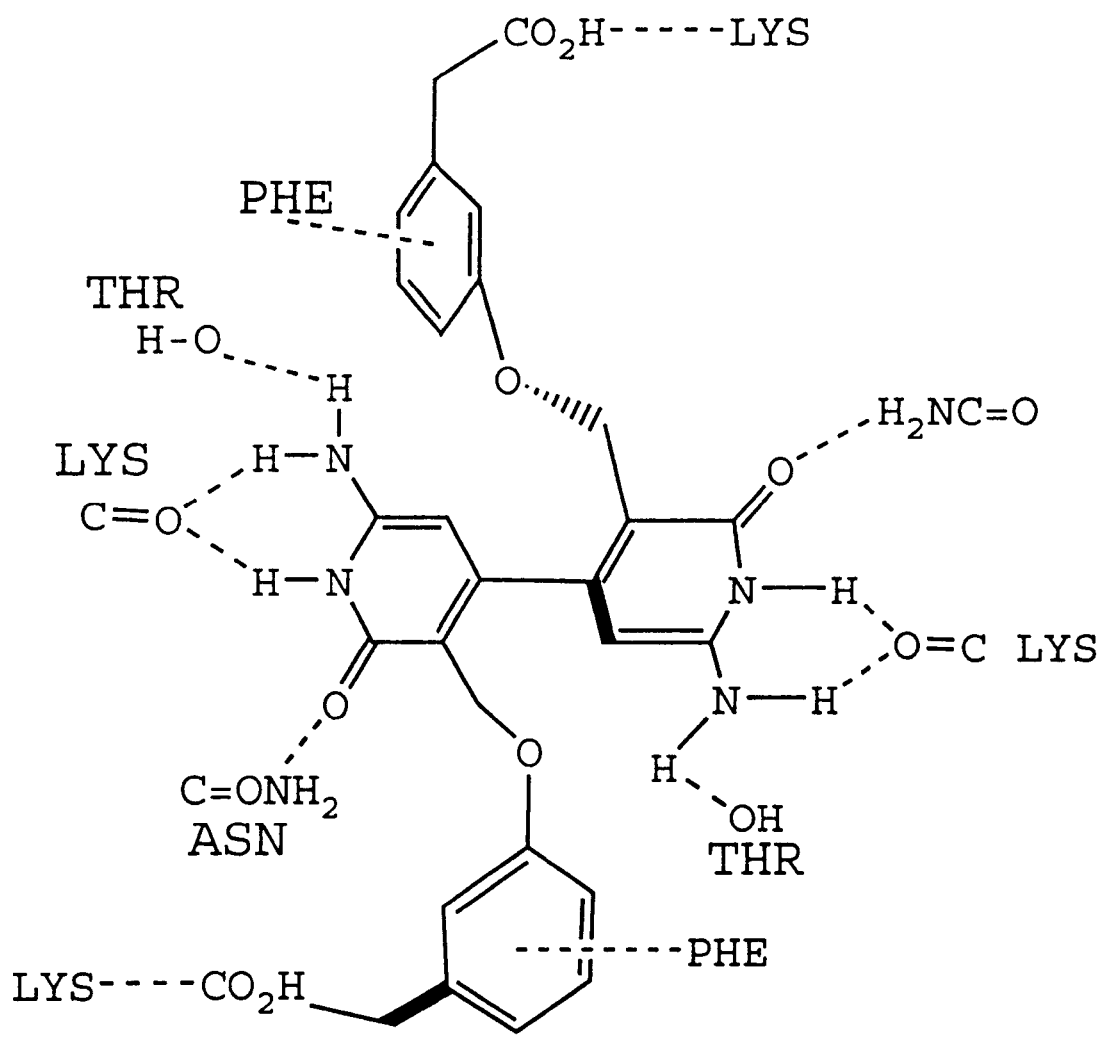
FIG. 4 is an illustration showing a various hydrogen bonding between the amino acids in FcγIIa receptor binding site and a particular modulator.

The present invention provides a variety of compounds which can modulate the interaction between Fc receptors and immunoglobulins. Without being bound by any theory, it is believed that particularly useful compounds target the region C (see FIG. 1) of Fc receptors, e.g., FcγRII. Thus, it is believed that these compounds interfere with the dimerization interface between two FcγRII proteins, thereby affecting cellular signal transduction through one or both of the FcR proteins. Specifically, it is believed that peptide residues 117–131 and 150–164 of FcγRII make up the interfacial area of the FcγIIa dimer, and compounds which can mimic or bind to these regions are believed to be good binding modulators. For example, native hexapeptide Phe121 to Ser126 or shorter segments span a region with significant hydrogen bonding interaction and therefore, are suitable modulators of dimerization between two FcγRIIa molecules. Such a protein segment is disclosed as part of SEQ ID No. 3 in U.S. patent application Ser. No. 09/245,764, filed Feb. 5, 1999, entitled "3 Dimensional Structure and Models of Fc Receptors and Uses Thereof," which is incorporated by reference herein in its entirety.

The compounds of the present invention are derived from a random screening as well as a rational drug design to modulate Fc receptors. FcγR are expressed on most hematopoietic cells, and through the binding of IgG play a key role in homeostasis of the immune system and host protection against infection. FcγRII is a low affinity receptor for IgG that essentially binds only to IgG immune complexes and is expressed on a variety of cell types including, for example monocytes, macrophages, neutrophils, eosinophils, platelets and B lymphocytes. FcγRII is involved in various immune and inflammatory responses including antibody-dependent cell-mediated cytotoxicity, clearance of immune complexes, release of inflammatory mediators and regulation of antibody production.

The binding of IgG to a FcγR can lead to disease indications that involve regulation by FcγR. For example, the autoimmune disease thrombocytopenia purpura involves tissue (platelet) damage resulting from FcγR-dependent IgG immune complex activation of platelets or their destruction by FcγR+ phagocytes. In addition, various inflammatory diseases are known to involve IgG immune complexes (e.g. rheumatoid arthritis, systemic lupus erythematosus), including type II and type III hypersensitivity reactions. Type II and type III hypersensitivity reactions are mediated by IgG, which can activate either complement-mediated or phagocytic effector mechanisms, leading to tissue damage.

Knowledge of the three dimensional structure of FcγRIIa or indeed any FcR can facilitate the formulation of therapeutic and diagnostic reagents for disease management. For example, by knowing the structure of a binding region of FcγRIIa, one can design compounds that can modulate the binding of immunoglobulins to FcγRIIa. The structure of a number of Fc receptors, including FcγRIIa, FcεRI and FcγRIIIb, are disclosed in provisional U.S. patent application Ser. No. 60/073,972, filed Feb. 6, 1998, which is incorporated by reference herein in its entirety, and the above mentioned U.S. patent application Ser. No. 09/245,764, filed Feb. 5, 1999, entitled "3 Dimensional Structure and Models of Fc Receptors and Uses Thereof."

FcγRIIa is a protein dimer and has a C2 axis of symmetry. A schematic structure of the binding region of FcγRIIa based on the X-ray crystal structure is shown in FIG. 1. Without being bound by any theory, it is believed that sites A and A' are believed to be the Fc-antibody interface regions; therefore, a compound which binds to or impinges on sites A or A' is likely to interfere with the normal binding of this receptor to IgG. In addition, a compound that binds to sites B, C and/or D may interfere with or facilitate antibody binding if the compound alters the structure of the receptor so as to destabilize antibody binding or encourage dimerization of the receptors, respectively.

FIG. 2 shows a lateral schematic view of site B, i.e., the groove, illustrating only one face, with the protein residues of interest in modulator design. The lip of the groove contains lysine and histidine residues and represents a target for interaction with hydrogen-bonding and/or acidic groups in a suitable modulator. The wall of the groove contains a phenylalanine benzene ring and may be a target for a hydrophobic interaction, particularly π—π interactions. The "floor" of the groove includes Phe121, Thr152, Leu159 and Ser161 and together with Asn154, Lys117 (backbone carbonyl) and Thr119. These proteins are believed to be arranged to form a pocket that is capable of strong hydrogen bonding and/or Van der Waals interactions with a modulator or a ligand.

The features of the groove detailed above have lead to the design and synthesis of compounds depicted generally as:

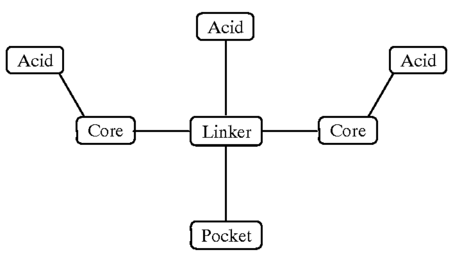

where the "core" is a lipophilic group, such as an aromatic ring, and "linker" represents connectivity of from 1 to about 20 atoms, preferably from 1 to about 10 atoms, and more preferably from 2 to about 8 atoms. The presence of the acid and the pocket groups which are directly linked to the linker group is optional. In order to interact favorably with the basic groups, e.g., Lys117 and His131, at the lip of the groove, acidic groups ("acid" ) can be branched from the "core" and/or the "linker". "Pocket" represents that portion of the molecule which fills the pockets at the floor of the groove. Alternatively, the modulator can bind or occupy only the pocket of the receptor. These principles are specifically exemplified in FIG. 3 which depicts how a particular modulator relates to the general design illustrated above and in FIG. 4 which illustrates the points of interaction between this modulator and the FcγRIIa protein.

An exemplary compound containing a "pocket" residue is shown in FIG. 3, where a cytosine-like ring moiety is present in the linker portion of the compound. Other suitable pocket binders include nucleic acids and related structures such as hydrazides and amidoureas as shown below or their derivative.

X is C=O or $CH_2$ hydrazides amidoureas

Preferably, these pocket residues consist of a dimer of a compound, e.g., a dimer of nucleic acids, hydrazides, amidoureas or their derivatives.

Compounds of the present invention which have the above described general features include an aromatic compound of the formula:

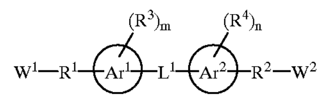

a heteroaromatic compound of the formula:

a cyclic compound of the formula:

a bicyclic compound of the formula:

and an amino acid derivative of the formula:

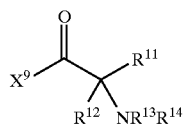

or salts thereof, where each of $W^1$ and $W^2$ is independently $CO_2R^{15}$, $C(=NH)NH(OH)$, $SO_3R^{15}$, $C(=NH)NH_2$, $OPO(OR^{15})_2$, $C(=O)CF_3$ or $PO(OR^{15})_2$; each of $Ar^1$, $Ar^2$, $Ar^4$ and $Ar^5$ is independently $C_6$–$C_{20}$ aryl or $C_1$–$C_{20}$ heteroaryl; $Ar^3$ is $C_1$–$C_{20}$ heteroaryl; each of $X^1$, $X^2$, $X^3$, $X^4$, $X^5$, $X^6$, $X^7$ and $X^8$ is independently methylene, O, S or $NR^{16}$; each of $R^1$ and $R^2$ is independently a bond, $C_1$–$C_6$ alkylene, or halogenated $C_1$–$C_6$ alkylene; each of $R^3$ and $R^4$ are independently halogen, —$Z^1$ or $C_1$–$C_6$ alkyl; each of $X^9$, $Y^1$ and $Z^1$ is independently $OR^{17}$, $SR^{17}$ or $NR^{17}R^{18}$; each of $R^5$ and $R^6$ is independently amino acid side chain residue or a moiety of the formula —$R^{19}$—$W^3$; each of $R^8$, $R^9$ and $R^{11}$ is independently an amino acid side chain residue, provided $R^{11}$ is not H or $CH_3$; $R^7$ is $OR^{20}$, $NR^{21}R^{22}$, or from about 1 to about 10 amino acids; $R^{10}$ is $C_1$–$C_6$ alkylene; $R^{12}$ is $C_1$–$C_6$ alkyl or $C_6$–$C_{20}$ aralkyl; $W^3$ is $C(=O)X^{10}$; $X^{10}$ is $OR^{23}$ or $NR^{24}R^{25}$; each of $R^{13}$, $R^{15}$, $R^{17}$, $R^{18}$, $R^{20}$, $R^{21}$, $R^{23}$ and $R^{24}$ is independently hydrogen or $C_1$–$C_6$ alkyl; each $R^{16}$ is independently H, $C_6$–$C_{20}$ aryl or an amide protecting group; $R^{19}$ is $C_1$–$C_6$ alkylene; each of $R^{22}$ and $R^{25}$ is independently H, $C_1$–$C_6$ alkyl or an amide protecting group; $R^{14}$ is H, $C_1$–$C_6$ alkyl or an amine protecting group; L is a linker comprising from 1 to about 20 atoms; and each of m and n is independently an integer from 0 to 2.

"Alkyl" groups according to the present invention are aliphatic hydrocarbons which can be straight or branched chain groups. Alkyl groups optionally can be substituted with one or more substituents, such as a halogen, alkenyl, alkynyl, aryl, hydroxy, amino, thio, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, fluoromethyl, difluoromethyl, trifluoromethyl, chloromethyl, trichloromethyl, methoxy ethyl, aminomethyl, and pentafluoroethyl.

"Aryl" groups are monocyclic or bicyclic carbocyclic or heterocyclic aromatic ring moieties. Aryl groups can be substituted with one or more substituents, such as a halogen, alkenyl, alkyl, alkynyl, hydroxy, amino, thio, alkoxy or cycloalkyl.

"Mono-aryl or heteroaryl" refers to a monocyclic carbocyclic or heterocyclic aromatic ring. Exemplary monoaryl or heteroaryl rings include pyrrole, thiophene, furan, imidazole, pyrazole, 1,2,4-triazole, pyridine, pyrazine, pyrimidine, pyridazine, thiazole, isothiazole, oxazole, isoxazole, s-triazine and benzene. Preferred group is phenyl.

"Di-aryl or heteroaryl" means a bicyclic ring system composed of two fused carbocyclic and/or heterocyclic aromatic rings. Exemplary di-aryl or heteroaryl rings include indene, isoindene, benzofuran, dihydrobenzofuran, benzothiophene, indole, 1H-indazole, indoline, azulene, tetrahydroazulene, benzopyrazole, benzoxazole, benzoimidazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benisoxazine.

"Aralkyl" refers to an alkyl group substituted with an aryl group. Suitable aralkyl groups include, without limitation, benzyl, 2-phenylethyl and picolyl. Aryl groups may also be substituted with other suitable functional groups. Aralkyl groups include those with heterocyclic and carbocyclic aromatic moieties.

A "linker" ($L^1$) refers to a chain of atoms which links $Ar^1$ to $Ar^2$ with the number of atoms as specified. The number associated with the linker refers to only the number of atoms which directly link $Ar^1$ and $Ar^2$. The $L^1$ moiety can contain groups that can participate in hydrogen bonding and/or Van der Waals interactions with amino acid residues in the groove of the receptor, for example, trifluoroacetyl, imide, urea, amidine, amidoxime or their derivatives.

An "amino acid sidechain residue" refers to an amino acid side chain which is found on the α-carbon of an α-amino acids of naturally occurring and commercially available amino acids. Typical amino acid sidechain residues include hydrogen (glycine), methyl (alanine), —$CH_2CH_2CH_2NHC(=NH)NH_2$ (arginine), —$CH_2C(=O)NH_2$ (asparagine), —$CH_2CO_2H$ (aspartic acid), —$CH_2SH$ (cysteine), —$CH_2CH_2C(=O)NH_2$ (glutamine), —$CH_2CH_2CO_2H$ (glutamic acid), —$CH_2$-(4-imidazole) (histidine), —$CH(Et)CH_3$ (isoleucine), —$CH_2CH(CH_3)$ (leucine), —$(CH_2)_4NH_2$ (lysine), —$(CH_2)_2SCH_3$ (methionine), —$CH_2Ph$ (phenylalanine), —$CH_2$—$CH_2$—$CH_2$-(proline), —$CH_2OH$ (serine), —$CH(OH)CH_3$ (threonine), —$CH_2$-(3-indole) (tryptophan), —$CH_2$-(4-hydroxyphenyl) (tyrosine) and —$CH(CH_3)_2$ (valine).

The pKa of corresponding acid group of $W^1$ and $W^2$ are less than about 9, more preferably less than about 7 and most preferably less than about 5. The "corresponding acid group of $W_1$ and $W_2$" refers to the parent acid group of $W^1$ and $W^2$, for example, when $W^1$ and $W^2$ are esters the corresponding acid refers to the carboxylic acid, and when $W^1$ and $W^2$ are alkyl phosphonates the corresponding acid refers to the phosphonic acid. It will be appreciated that the pKa of $W^1$ and $W^2$ depends not only on the identity of $W^1$ and $W^2$ but also on the type of substituents present near the $W^1$ and $W^2$ groups and/or in the mono- or di-aryl or heteroaryl group to which $W^1$ and $W^2$ are attached. Thus, for example, a presence of one or more electron withdrawing groups such as nitro, nitroso, carbonyl, cyano and halogen groups reduces the pKa of the corresponding $W^1$ and $W^2$ acid group. The pKa is defined as -log(Ka) where Ka is a dissociation constant. The strength of an acid or base in a given medium is indicated by the value of its dissociation constant. For example, strong bases are strong proton acceptors (or an electron-pair donor) and have high pKa values. pKa values depend on a variety of factors such as solvent and temperature. For example, water ($H_2O$), not the conjugate acid of water which is $H_3O^+$, has pKa of 15.7 at 250° C. in water, 16.7 at 0° C., and 14.7 at 60° C. In addition, its pKa is 27.5 in dimethyl sulfoxide (DMSO) at 25° C. The pKa values in the present application refer to the pKa values relative to pKa value of water at about 15.7, unless otherwise stated.

With reference to the formulas described herein:
Preferably, $W^1$ and $W^2$ are independently $CO_2R^5$, $C(=NH)NH(OH)$ $OPO(OR^5)_2$, $C(=O)CF_3$ or $PO(OR^5)_2$.

Preferably, $R^1$ and $R^2$ are independently a bond, $C_1$–$C_6$ alkylene or fluorinated $C_1$–$C_6$ alkylene. More preferably, $R^1$ and $R^2$ are independently a bond, methylene or difluoromethylene.

Preferably, each of $Ar^1$, $Ar^2$ and $Ar^5$ are independently mono-aryl or heteroaryl. More preferably $Ar^1$, $Ar^2$ and $Ar^5$ are phenyl.

Preferably, $Ar^3$ is 2-pyridonyl, and more preferably $Ar^3$ is 4-$Ar^4$-(2-pyridonyl), i.e., the 4-position of the 2-pyridone moiety is attached to the $Ar^4$ moiety.

Preferably, $Ar^4$ is $C_1$–$C_{20}$ heteroaryl. More preferably, $Ar^4$ is pyridyl. Most preferably $Ar^4$ is 4-pyridyl, i.e., the 4-position of the pyridine moiety is attached to the $Ar^3$ moiety.

Preferably, $Y^1$ is $NR^{17}R^{18}$. More preferably, $Y^1$ is $NH_2$.

Preferably, each $R^{15}$ is independently hydrogen, methyl or ethyl.

Preferably, $L^1$ is $C_1$–$C_6$ alkylene; $C_1$–$C_6$ alkenylene, including αβ-unsaturated carbonyl moieties (e.g., —CH=CH—C(=O)—); or a moiety of the formula —$R^{33}$—$X^{14}$—, —$R^{34}$—$X^{15}$—$R^{35}$— or —$X^{16}$—$R^{36}$—$Ar^6$—$Ar^7$—$R^{37}$—$X^{17}$—. Each of $R^{33}$, $R^{34}$, $R^{35}$, $R^{36}$ and $R^{37}$ is independently $C_1$–$C_6$ alkylene (including a substituted alkylene), preferably methylene. Each of $X^{14}$, $X^{15}$, $X^{16}$ and $X^{17}$ is independently O, S or $NR^{38}$, preferably O or $NR^{38}$. Each of $Ar^6$ and $Ar^7$ is independently $C_6$–$C_{20}$ aryl or $C_1$–$C_{20}$ heteroaryl, preferably 2-pyridone. And $R^{38}$ is H, $C_1$–$C_6$ alkyl or an amine protecting group, preferably —$CH_2CO_2H$. More preferably, $L^1$ is sulfonamide (—$SO_2NH$—), ethylene (—$CH_2CH_2$—), —$CH_2O$—, —CH=CHC(=O)—, —$CH_2CH_2CH(OH)$—, —CH=CH—, —CH(OH)CH(OH)—, —$CH_2N(R^{38})CH_2$—, a moiety of the formula:

or a moiety of the formula:

where each of $R^{27}$ and $R^{28}$ is independently H, $C_1$–$C_6$ alkyl, $C_6$–$C_{10}$ aralkyl or a protecting group. Preferably $R^{27}$ and $R^{28}$ are independently H or a protecting group. More preferably, $R^{27}$ and $R^{28}$ are independently H or 4-methoxybenzyl.

Preferably m and n are 0.

Alternatively, $R^1$ and $W^1$ and/or $R^2$ and $W^2$ together form —$(CH_2)_a$CH($NHR^{29}$)$CO_2R^{39}$ and —$(CH_2)_b$CH($NHR^{30}$)$CO_2R^{40}$, respectively, where a and b are independently an integer from 0 to 2, $R^{29}$ and $R^{30}$ are independently H or an amine protecting group, and $R^{39}$ and $R^{40}$ are independently H or $C_1$–$C_6$ alkyl. Preferably, a and b are 1. Preferably, $R^{29}$ and $R^{30}$ are independently H, $C_1$–$C_6$ alkyl or an amine protecting group.

Preferably, $R^5$ is asparagine sidechain residue.

Preferably, $R^6$ is glutamine sidechain residue.

Preferably, $R^7$ is from about 1 to about 10 amino acids or derivatives thereof, more preferably from about 1 to about 5 amino acids or derivatives thereof, still more preferably at least about 2 amino acid residues or derivatives thereof, and most preferably -lys-ser-$CONHCH_3$ moiety, i.e., a moiety of the formula —NHCH[$(CH_2)_4NH_2$]CONHCH($CH_2OH$)$CONHCH_3$.

Preferably, $X^1$, $X^2$, $X^3$, $X^4$, $X^5$, $X^6$, $X^7$ and $X^8$ are independently O or $NR^{16}$. More preferably, $X^1$, $X^2$, $X^3$, $X^4$, $X^5$, $X^6$, $X^7$, and $X^8$ are $NR^{16}$.

Preferably, $X^9$ is $OR^{17}$ or $NR^{17}R^{18}$, more preferably $NR^{17}R^{18}$, and most preferably $NH_2$.

Preferably, $R^8$ is glycine sidechain residue (i.e., H).

Preferably, $R^9$ is tyrosine sidechain residue (i.e., 4-hydroxybenzyl).

Preferably, $R^{10}$ is propylene.

Preferably, $R^{11}$ is lysine side chain residue, i.e., a moiety of the formula —$(CH_2)_4NH_2$.

Preferably $R^{12}$ is $C_6$–$C_{20}$ aralkyl, and more preferably 2-phenylethyl.

Preferably $R^{13}$ is H.

Preferably $R^{14}$ is H or an amine protecting group, more preferably an amine protecting group, and most preferably an acetyl group, i.e., a moiety of the formula —C(=O)$CH_3$.

Preferably, each $R^{16}$ is independently H or $C_6$–$C_{20}$ aryl. More preferably each $R^{16}$ is independently H or phenyl.

In one particular embodiment of the present invention, the aromatic compound described above is of the formula:

More preferably, the aromatic compound is of the formula:

In another particular embodiment of the present invention, the aromatic compound described above is of the formula:

In one particular embodiment of the present invention, the heteroaromatic compound described above is of the formula:

More preferably, the heteroaromatic compound described above is of the formula:

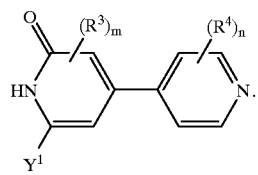

In another particular embodiment of the present invention, the cyclic compound described above is of the formula:

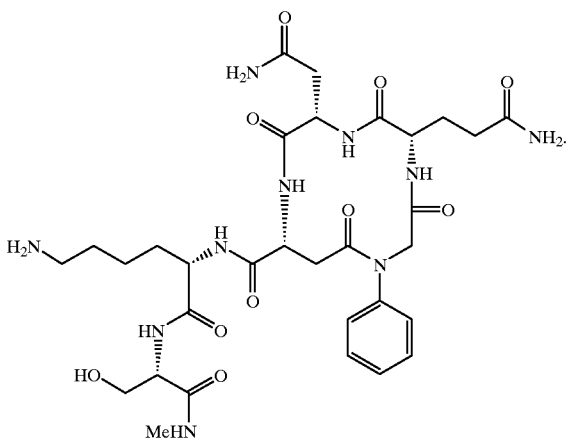

In still another particular embodiment of the present invention, the bicyclic compound described above is of the formula:

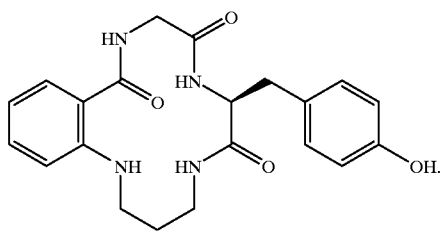

In yet another particular embodiment of the present invention, the amino acid derivative described above is of the formula:

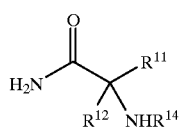

or its salt thereof. Preferably, the amino acid derivative described above is of the formula:

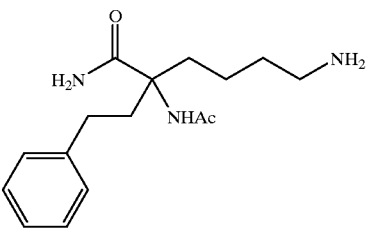

or its salt thereof.

The Fc receptor modulating compounds of the present invention can also include nucleosides or derivatives thereof. Preferably, the nucleosides of the present invention have the formula:

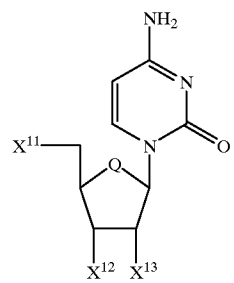

where Q is O or methylene. Preferably, Q is O. $X^{11}$ is $OR^{31}$ or $OPO(OR^{31})_2$. Preferably $X^{11}$ is OH or $OPO_3H_2$. Each of $X^{12}$ and $X^{13}$ is independently H or $OR^{15}$. Preferably, each of $X^{12}$ and $X^{13}$ is independently H or OH. Each of $R^{31}$ and $R^{32}$ is independently H or $C_1$–$C_6$ alkyl.

The Fc receptor modulating compounds of the present invention can further include folic acid or its derivatives.

The Fc receptor modulating compounds of the present invention can also include peptides which can modulate the interaction between Fc receptors and immunoglobulins. Without being bound by any theory, it is believed that particularly useful peptides target the region C (see FIG. 1) of Fc receptors, e.g., FcγRII. Thus, it is believed that these peptides interfere with the dimerization interface between two FcγRII proteins, thereby affecting cellular signal transduction through one or both of the FcR proteins. Specifically, residues 117–131 and residues 150–164 make up the interfacial area of the FcγIIa dimer, and peptides from these sequences or their mimics are binding inhibitors. For example, native hexapeptide Phe121to Ser126 or shorter segments spans a region with significant hydrogen bonding interaction and therefore, is a suitable modulator of dimerization between two FcγRIIa molecules. Such a protein segment is disclosed as part of SEQ ID No. 3 in the above mentioned U.S. patent application Ser. No. 09/245,764, filed Feb. 5, 1999, entitled "3 Dimensional Structure and Models of Fc Receptors and Uses Thereof." Thus, the present inventors have discovered that a tripeptide of sequence GKS (gly-lys-ser) or its derivatives and hexapeptides of sequence FQNGKS (phe-gln-asn-gly-lys-ser) or derivatives thereof modulate binding of FcγRII to IgG. See Example 24 and FIGS. 10 and 11.

The present inventors have also found that conformationally constrained macrocyclic compounds modulate FcR protein activities. As used herein a "macrocyclic compound" refers to a compound containing a ring moiety which is comprised of from about 8 atoms to about 18 atoms.

Preferably, the ring structure of the macrocyclic compound of the present invention comprises from about 10 to about 16 atoms, more preferably from about 12 to about 14 atoms, and most preferably from about 13 to about 14 atoms. A particularly useful macrocyclic compound of the present invention is a cyclic peptide or derivatives thereof. Such cyclic peptide having the formula:

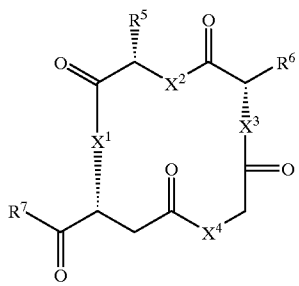

is described above.

The top of the FG loop of FcR has been shown by mutagenesis studies to be important in Ig binding. The FG peptide strand contains an extended β-sheet which projects the amino acid sidechains in the FG loop in a defined orientation. Such Fc protein orientation is described in the above mentioned U.S. patent application Ser. No. 09/245,764, filed Feb. 5, 1999, entitled "3 Dimensional Structure and Models of Fc Receptors and Uses Thereof." Molecules which can act as β-turn mimics so as to present its sidechains at the top of the FG loop in the same way as those in the receptor have also been found to be effective in modulating the FcR receptor activities. Thus, in another embodiment of the present invention, the Fc receptor modulating compound of the present invention also includes a compound of the formula:

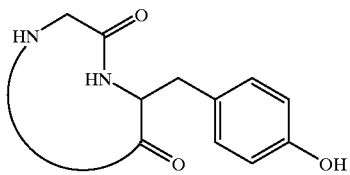

where the macrocyclic portion contains the same number of atoms as described above. One particular embodiment of such β-turn mimic is the compound described above having the formula:

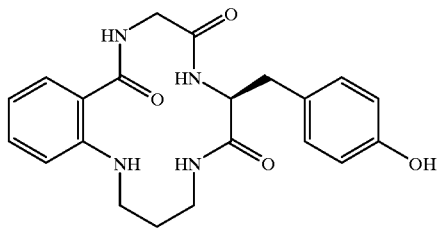

The compounds of the present invention can be synthesized from readily available starting materials. Various substituents on the compounds of the present invention can be present in the starting compounds, added to any one of the intermediates or added after formation of the final products by known methods of substitution or conversion reactions.

If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by T. W. Green, John Wiley and Sons, 1981, which is incorporated herein in its entirety. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono-and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Since the compounds of the present invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent on the ring involved.

It is to be understood that the scope of this invention encompasses not only the various isomers which may exist but also the various mixtures of isomers which may be formed.

If the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety. Basically, the resolution of the compounds is based on the differences in the physical properties of diastereomers by attachment, either chemically or enzymatically, of an enantiomerically pure moiety results in forms that are separable by fractional crystallization, distillation or chromatography.

When the compound of the present invention contains an olefin moiety and such olefin moiety can be either cis- or trans-configuration, the compound can be synthesized to produce cis- or trans-olefin, selectively, as the predominant product. Alternatively, the compound containing an olefin moiety can be produced as a mixture of cis- and trans-olefins and separated using known procedures, for example, by chromatography as described in W. K. Chan, et al., *J. Am. Chem. Soc.,* 1974, 96, 3642, which is incorporated herein in its entirety.

The compounds of the present invention form salts with acids when a basic amino function is present and salts with bases when an acid function, e.g., carboxylic acid or phosphonic acid, is present. All such salts are useful in the isolation and/or purification of the new products. Of particular value are the pharmaceutically acceptable salts with both acids and bases. Suitable acids include, for example, hydrochloric, oxalic, sulfuric, nitric, benzenesulfonic, toluenesulfonic, acetic, maleic, tartaric and the like which are pharmaceutically acceptable. Basic salts for pharmaceutical use include Na, K, Ca and Mg salts.

In addition to and/or instead of a rational drug design, other Fc receptor modulators can be identified by a screening process, where a variety of compounds are tested to determine their Fc receptor modulating activity. In this manner, a variety of Fc receptor modulators have been identified. Thus, compounds of the present invention include substituted and unsubstituted benzoic acids, in particular, 4-methyl benzoic acid and 3-methyl benzoic acid; nucleosides and analogs thereof; and folic acid and its derivatives.

The compounds of the present invention are Fc receptor modulators, e.g., they modulate Fc receptor binding of immunoglobulins. Preferably, the compounds of the present invention modulate Fc receptors selected from the group consisting of FcαR, FcεR, FcγR and mixtures thereof, more preferably from the group consisting of FcγRI, FcγRII, FcγRIII and mixtures thereof, still more preferably from the group consisting of FcγRIIa, FcγRIIb, FcγRIIc and mixtures thereof, and most preferably FcγRIIa receptor. The compounds of the present invention can be used in a variety of applications including treatment or diagnosis of any disease where aggregates of antibodies are produced and where immune complexes are produced by contact of antibody with intrinsic or extrinsic antigen. Exemplary treatments and diagnosis applicable by the compounds of the present invention include immune complex diseases; autoimmune diseases including but not limited to rheumatoid arthritis, systemic lupus erythematosus, immune thrombocytopenia, neutropenia, hemolytic anaemias; vasculitities including but not limited to polyarteritis nodosa, systemic vasculitis; xenograft rejection; and infectious diseases where FcR uptake of virus enhances infection including but not limited to flavivirus infections such as Dengue virus-dengue hemorrhagic fever and measles virus infection. The compound of the present invention can also be used to reduce IgG-mediated tissue damage and to reduce inflammation.

The compounds of the present invention can also enhance leukocyte function by enhancing FcR function. These functions include antibody dependent cell mediated cytotoxicity, phagocytosis, release of inflammatory cytokines. Exemplary treatments and diagnosis for enhanced FcR function include any infection where normal antibodies are produced to remove the pathogen; and any disease requiring FcR function where natural or recombinant antibodies can be used in treatment such as cancer and infections, for example, the antibody can be administered in combination with the compound of the present invention to enhance the effect of the antibody treatment.

The compounds of the present invention can be administered to a patient to achieve a desired physiological effect. Preferably the patient is an animal, more preferably a mammal, and most preferably a human. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Preferred compositions or preparations according to the present invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation.

The active compound can also be administered parenterally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of the present invention can be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2x to about 4x, may be required for oral administration.

Additional objects, advantages, and novel features of this invention will become apparent to those skilled in the art upon examination of the following examples thereof, which are not intended to be limiting.

Experimental

The following abbreviations and terms are used herein:

rt room temperature
$Et_2O$ diethyl ether (i.e., ether or ethyl ether)
MS (APCI) atmospheric pressure chemical ionization
THF Tetrahydrofuran
EtOAc Ethyl acetate
TMSCl Trimethylsilyl chloride
$CH_3CN$ Acetonitrile
DMF Dimethylformamide Experiment 1

This experiment illustrates a synthesis of 1,2-Bis(m-carboxyphenyl)ethane:

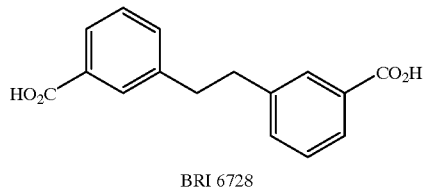

BRI 6728

Step 1: 1,2-Bis(m-bromophenyl)ethane was prepared by the method of Lindsay et al (JACS, 1961, 83, 943) as follows. Magnesium (0.05 g, 2.0 mmol) was added to a solution of 3-bromobenzylbromide (1.0 g, 4.0 mmol) in $Et_2O$ (10 mL) at rt. After 20 min at room temperature all the magnesium had dissolved and anhydrous ferric chloride (5 mg) was added. The reaction was heated to reflux for 1 hour, cooled, acidified to about pH 1 with 1 M aqueous $H_2SO_4$ and extracted with $Et_2O$ (3×50 mL). The combined organic extracts were washed with water (50 mL), dried ($Na_2SO_4$), filtered and concentrated in vacuo to give a yellow solid. Recrystallization from petroleum ether gave 1,2-bis(m-bromophenyl)ethane as a colorless solid. MS (APCI) m/z 338 (50%), 340 (100), 342 (50). $^1$H NMR (200 MHz, $CDCl_3$): δ2.85, s, 2H; 7.02–7.25, m, 2H; 7.30–7.39, m, 2H.

Step 2: tert-Butyl lithium (2.1 mL of 1.7 M solution in pentane, 3.60 mmol) was added dropwise to a solution of 1,2-bis(m-bromophenyl)ethane (305 mg, 0.90 mmol) in THF (10 mL) at −78° C. After 20 min at this temperature, $CO_2$ was bubbled through the reaction mixture while the cooling bath was removed and the reaction mixture reach rt. The reaction mixture was partitioned between water (50 mL) and $Et_2O$ (50 mL) and aqueous phase was separated and acidified to about pH 1 with concentrated aqueous HCl keeping the internal temperature below 25° C. The aqueous phase was extracted with EtOAc (3×50 mL) and the combined organic extracts dried ($Na_2SO_4$), filtered and concentrated in vacuo to give 1,2-bis(m-carboxyphenyl)ethane as a white solid. MS (APCI) m/z 269 (M+1, 100%) $^{13}$C NMR (50 MHz, $d_6$-DMSO): δ38.4, 128.8, 130.3, 131.1, 132.5, 134.8, 143.5, 169.2. The melting point agreed with that reported by Lindsay et al (JACS, 1961, 83, 943).

Experiment 2

This experiment illustrates a synthesis of 3-[(m-carboxyphenyl)methoxy]benzoic acid:

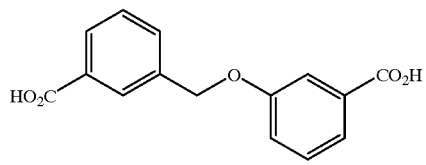

BRI 6727

Step 1: A mixture of 3-bromophenol (13.8 g, 80 mmol), 3-bromobenzyl bromide (10 g, 40 mmol), $K_2CO_3$ (16.6 g. 120 mmol) and NaI (300 mg, 2 mmol) in acetone (100 mL) was heated to reflux for 12 hours. The reaction mixture was cooled to rt, concentrated in vacuo and partitioned between $Et_2O$ (300 mL) and water (300 mL). The organic phase was washed with aqueous NaOH (1 M, 300 mL), dried ($Na_2SO_4$), filtered and concentrated in vacuo to give 3-[(m-bromophenyl)methoxy]bromobenzene as a clear oil. MS (APCI) m/z 339 ($M^+$−3, 50%), 341 ($M^+$−1, 100%), 343 ($M^+$+3, 50%), $^{13}$C NMR (50 MHz, $CDCl_3$); δ68.9, 113.4, 117.9, 122.5, 122.6, 124.1, 125.6, 129.9, 130.0, 130.4, 130.9, 138.4, 158.9.

Step 2: Using 3-[(m-bromophenyl)methoxy]bromobenzene and the method described in Example 1, step 2 gave 3-[(m-carboxyphenyl)methoxy]-benzoic acid as a white solid. MS (APCI) m/z 271 (M$^+$−1, 100%). $^{13}$C NMR (50 MHz, d$_6$-DMSO): δ68.3, 114.5, 119.3, 121.5, 127.8, 128.3, 129.3, 130.5, 131.5, 131.8, 137.0, 157.7, 166.6, 166.7.

Experiment 3

This experiment illustrates a synthesis of 1,2-bis(3-phosphono-phenyl)ethane:

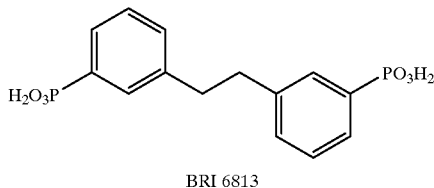

BRI 6813

Step 1: 1,2-Bis(3-bromophenyl)ethane (obtained using the method of Example 1, step 1) (440 mg., 1.29 mmol), diethyl phosphite (0.46 mL, 3.59 mL) and triethylamine (0.5 mL, 3.59 mmol) were dissolved in toluene and degassed. Pd(PPh$_3$)$_4$ (185 mg, 0.16 mmol) was added in one portion and the reaction heated to 90° C. for 16 hours. The reaction was cooled to room temperature and purified by column chromatography (SiO$_2$, 50% EtOAc in petroleum ether→100% EtOAc→100% EtOH) to give 1,2-bis[3-(diethoxyphosphono)phenyl]-ethane as a white solid. MS (APCI) m/z 455 (M$^+$+1, 100%). $^{31}$P NMR (81 MHz, proton decoupled, CDCl$_3$): δ+19.5.

Step 2: Trimethylsilylbromide (1.03 mL, 7.8 mmol) was added dropwise to a solution of the above ester (586 mg, 1.30 mmol) in CH$_2$Cl$_2$ (10 mL) at rt. The reaction was stirred for 16 hours at room temperature and concentrated in vacuo. MeOH (5 mL) was added and the solution concentrated in vacuo. This procedure was repeated a further two times to give 1,2-bis(3-phosphonophenyl)ethane as a white solid. MS (APCI) m/z. 341 (M$^+$−1, 100%). $^{31}$P NMR (81 MHz, proton decoupled, CDCl$_3$): δ+14.6.

Experiment 4

This experiment illustrates a synthesis of 3,3'-Dicarboxychalcone:

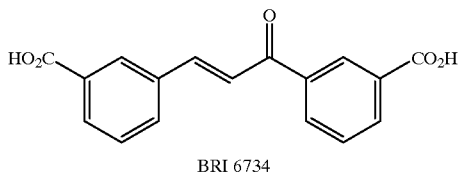

BRI 6734

Step 1: 3-Cyanobenzaldehyde (3.0 g, 23.0 mmol) and 3-cyanoacetophenone (3.34 g, 23.0 mmol) in glacial acetic acid (5 mL) and concentrated H$_2$SO$_4$ (3.66 mL, 69 mmol) was stirred at room temperature for 72 hours. Water (200 mL) was added and the reaction filtered. The precipitate was washed with water (2×200 mL) and dried in vacuo to give 3,3'-dicyanochalcone as an off-white solid. MS (APCI) m/z 258 (M$^+$−1, 100%). $^{13}$C NMR (50 MHz, d$_6$-DMSO): δ111.7, 117.8, 118.0, 123.0, 129.7, 131.6, 132.1, 132.4, 133.3, 133.5, 135.3, 136.1, 137.4, 142.1, 187.3.

Step 2: A solution of 3,3'-dicyanochalcone from step 1 (2.0 g, 7.75 mmol) in glacial acetic acid (30 mL) was treated with a mixture of concentrated H$_2$SO$_4$ (10 mL) and water (10 mL). The reaction mixture was heated to 130° C. for 12 hours, cooled to room temperature and filtered. The precipitate was washed with water (3×100 mL) and dried in vacuo to give 3,3'-dicarboxychalcone as a yellow solid. MS (APCI) m/z 295 (M$^+$−1, 100%). $^{13}$C NMR (50 MHz, d$_6$-DMSO); δ122.5, 128.6, 128.7, 129.2, 130.8, 131.0, 131.2, 132.4, 132.5, 133.1, 134.5, 137.2, 143.1, 166.3, 166.5, 188.2.

Experiment 5

This experiment illustrates a synthesis of 1,3-bis (m-carboxy-phenyl)-1-propanol:

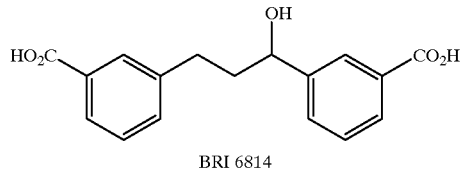

BRI 6814

3,3'-Dicarboxychalcone (Example 4, step 2) (430 mg, 1.45 mmol) in ethanol (10 mL) containing aqueous NaOH (1 M, 2.90 mmol) was hydrogenated at 45 psi for 48 hours in the presence of Wilkinson's catalyst (67 mg, 0.07 mmol). The reaction mixture was filtered and concentrated in vacuo. The residue was dissolved in methanol (10 mL) and treated with NaBH$_4$ (220 mg, 5.8 mmol) at rt. The reaction mixture was stirred for 16 hours at rt, quenched with the cautious addition of saturated aqueous NH$_4$Cl and partitioned between EtOAc (50 mL) and aqueous HCl (1 M, 50 mL). The organic extract was dried (Na$_2$SO$_4$), filtered and concentrated in vacuo to give 1,3-bis (m-carboxyphenyl)-1-propanol as a viscous oil. MS (APCI) m/z 299 (M$^+$−1, 100%). $^1$H NMR (200 MHz, CDCl$_3$); δ1.95–2.10, m, 2H; 2.68–2.83, m, 2H; 4.62–4.78, m, 1H; 7.03–7.60, m, 4H; 7.75–8.03, m, 4H.

Experiment 6

This experiment illustrates a synthesis of trans-3,3'-bis-carboxystilbene:

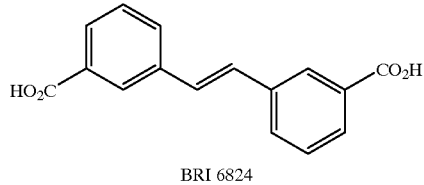

BRI 6824

Step 1: Methyl 3-bromobenzoate (21.5 g, 100 mmol), Pd(OAc)$_2$ (224 mg, 1 mmol), tri-o-tolylphosphine (608 mg, 2 mmol) and tributylamine (26.2 mL, 110 mmol) in DMF (100 mL) was degassed with argon and heated to 130° C. for 6 hours while a stream of ethylene was bubbled through the solution. The reaction mixture was cooled to room temperature and filtered. The precipitated was washed with cold Et$_2$O (2×50 mL) and dried in vacuo to give trans-3,3'-bis-carboxystilbene dimethyl ester as an off-white solid. $^{13}$C NMR (50 MHz, CDCl$_3$): δ52.2, 127.5, 128.8, 130.6, 130.9, 137.2, 166.9.

Step 2: The above diester (500 mg, 1.7 mmol) in the THF (10 mL) was treated at room temperature with aqueous LiOH (1 M, 10 mL). After stirring for 16 hours at rt, the reaction mixture was partitioned between Et$_2$O (50 mL) and water (50 mL). The aqueous phase was separated and the organic phase was extracted with water (25 mL). The combined aqueous extracts were acidified with concentrated aqueous (HCl while maintaining the internal temperature below 10° C. The aqueous phase was extracted with CH$_2$Cl$_2$ (3×50 mL) and the combined organic extracts dried (Na₂SO₄), filtered and concentrated in vacuo to give trans-3,3'-Biscarboxystilbene as a white solid. MS (APCI) m/z 267 (M⁺−1, 100%). ¹H NMR (200 MHz, d₆-DMSO): δ7.28–7.56, m, 2H; 7.78–7.90, m, 2H; 8.20, s, 1H.

Experiment 7

This experiment illustrates a synthesis of (S,S)-1,2-bis-(3-carboxyphenyl)ethane-1,2-diol:

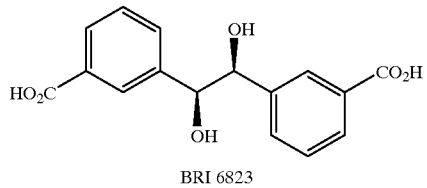

BRI 6823

Step 1: trans-3,3'-Biscarboxystilbene dimethyl ester (Example 6, step 1) (5.0 g, 16.9 mmol) and N-methylmorpholine-N-oxide (2.2 g, 18.6 mmol) in acetone (50 mL) and water (20 mL) were treated at room temperature with an aqueous solution of OsO₄ (4.3 mL, 39.4 mM, 0.17 mmol). The reaction mixture was stirred for 16 hours at rt, quenched by addition of sodium metabisulfite (3.0 g) and the pH adjusted to about pH 7 with 2 M aqueous sulfuric acid. The acetone was removed in vacuo and the remaining solution acidified to about pH 2, saturated with NaCl and extracted with EtOAc (3×100 mL). The combined organic extracts were dried (Na₂SO₄), filtered and concentrated in vacuo to give (R,R)-1,2-bis-[3-(carbomethoxy)phenyl]ethane-1,2-diol as a white solid. ¹H NMR (200 MHz, CDCl₃): δ3.2, bs, 1H; 3.82, s, 3H; 4.77, s, 1H; 7.20–7.31, m, 2H; 7.80–7.89, m, 2H.

Step 2: The above diester (500 mg, 1.5 mmol) was hydrolyzed using the procedure described in Example 6, step 2 to give (S,S)-1,2-bis-(3-carboxyphenyl)ethane-1,2-diol as a white solid. MS (APCI) m/z 301 (M⁺−1, 100%). ¹H NMR (200 MHz, d₆-DMSO): δ3.40, bs, 1H; 4.76, s, 1H; 5.56, bs, 1H; 7.20–7.29, m, 2H; 7.80–7.91, m, 2H.

Experiment 8

This experiment illustrates a synthesis of 3,3'-bis-(carboxy-methyl)stilbene:

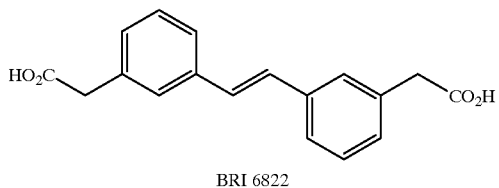

BRI 6822

Step 1: Methyl 3-bromophenylacetate (8.0 g, 34.9 mmol) was reacted with ethylene using the procedure described in Example 6, step 1. The crude reaction product was purified by column chromatography (SiO₂, 5% EtOAc in petroleum ether) to give 3,3'-bis-[(carbo-methoxy)methyl]stilbene and methyl 3-(ethenyl)phenyl-acetate as a white solid mixture.

3,3'-Bis-[(carbo-methoxy)methyl]stilbene: ¹H NMR (200 MHz, CDCl₃): δ3.65, s, 2H; 3.70, s, 3H; 7.1, s, 1H; 7.15–7.50, m, 4H. ¹³C NMR (50 MHz, CDCl₃): δ41.2, 52.1, 125.3, 127.4, 128.6, 128.7, 128.9, 134.4, 137.6, 171.9.

Methyl 3-(ethenyl)phenylacetate: ¹H NMR (200 MHz, CDCl₃): δ3.63, s, 2H; 3.68, s, 3H; 5.28, d, J=10.9 Hz, 1H; 5.78, d, J=18.8 Hz, 1H; 6.72, d, J=10.9, 18.8 Hz, 1H; 7.18–7.41, m, 4H Step 2: 3,3'-Bis-[(carbomethoxy)methyl]stilbene was hydrolyzed using the procedure described in Example 6, step 2 to give 3,3'-bis-[(carboxy)methyl]stilbene as a white solid. MS (APCI) m/z 295 (M⁺−1, 100%). ¹H NMR (200 MHz, d₆-DMSO): δ3.60, s, 2H; 7.00–7.62, m, 5H.

Experiment 9

This experiment illustrates a synthesis of 1,2-bis-[m-(carboxymethyl)phenyl]ethane:

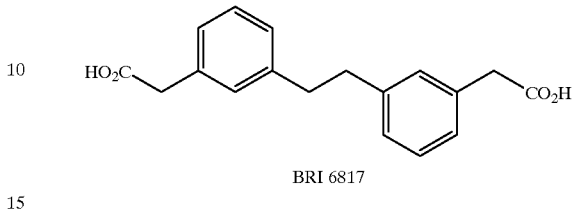

BRI 6817

Step 1: 3,3'-Bis-[(carbomethoxy)methyl]stibene (Example 8, step 1) (500 mg, 1.5 mmol) and palladium on carbon (10%, 200 mg) in methanol (20 mL) was hydrogenated under an atmosphere of hydrogen for 16 hours at rt. The reaction was filtered and concentrated in vacuo to give 1,2-bis-[m-(carbomethoxymethyl)phenyl]ethane as a colorless oil. ¹H NMR (200 MHz, CDCl₃): δ2.91, s, 2H; 3.63, s, 2H; 3.72, s, 3H; 7.08–7.31, m, 4H.

Step 2: The above ester was hydrolyzed using the procedure described in Example 6, step 2 to give 1,2-bis-]m-(carboxymethyl]ethane as a white solid. MS (APCI) m/z 297 (M⁺−1, 100%). ¹H NMR (200 MHz, d₆-DMSO): δ2.82, s, 2H; 3.56, s, 2H; 7.06–7.06–7.27, m, 4H; 12.25, bs, 1H.

Experiment 10

This experiment illustrates a synthesis of 1-[m-(carboxymethyl)phenyl]-2-[m-(carboxyhenyl)]ethane:

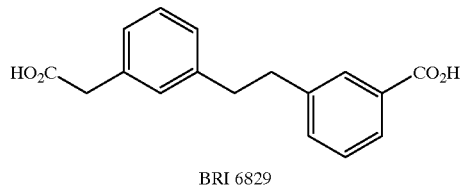

BRI 6829

Step 1: Methyl 3-(ethenyl)phenylacetate (Example 8, step 1) (1.1 g, 6.25 mmol), methyl 3-bromobenzoate (960 mg, 4.46 mmol), palladium acetate (20 mg, 0.09 mmol), N,N-dimethylglycine hydrochloride (249 mg, 1.78 mmol) and sodium acetate (731 mg, 8.92 mmol) were dissolved in N-methylpyrrolidinone, degassed with argon and heated to 130° C. for 5 hours. The reaction was cooled to rt, diluted with EtOAc (100 mL) and the organic phase washed with water (100 mL), aqueous HCl (1 M, 100 mL) and saturated aqueous NaHCO₃ (100 mL). The organic extracts were dried (Na₂SO₄), filtered and concentrated in vacuo to give trans-1-[m-(3-carbomethoxymethyl)phenyl]-2-[3-(carbomethoxy-phenyl)]ethane as a colorless oil. MS (APCI) m/z 309 (M⁺−1, 100%). ¹H NMR (200 MHz, CDCl₃): δ3.64, s, 2H; 3.68, s, 3H; 7.16–7.56, 6H; 7.63–7.71, m, 1H; 7.90–7.98, m, 1H; 8.20, m, 1H.

Step 2: The above compound was hydrogenated according to the method described in Example 9, step 1 to give 1-[m-(carbomethoxymethyl)-phenyl]-2-[m-(carbomethoxyphenyl)]ethane as a colorless oil. ¹H NMR (200 MHz, CDCl₃): δ2.87, m, 4H; 3.56 s, 2H; 3.60, s, 3H; 3.84, s, 3H; 6.95–7.36, 6H; 7.77–7.90, m, 2H.

Step 3: The ester in Step 2 was hydrolyzed using the procedure described in Example 6, step 2 to give 1-[m-(carboxymethyl)phenyl]-2-[m-(carboxyphenyl)]ethane as a white solid. MS (APCI) m/z 283 (M⁺−1, 100%). ¹H NMR (200 MHz, $d_6$-DMSO): δ2.92, m, 4H; 3.55, s, 2H; 7.02–7.35, m, 4H; 7.36–7.60, m, 2H; 7.71–7.93, m, 2H. $^{13}$C NMR (50 MHz, $d_6$-DMSO): δ38.6, 38.7, 40.9, 128.5, 128.8, 130.0, 130.3, 131.0 131.2, 132.6, 134.8, 136.7, 143.1, 143.8, 169.2, 174.5.

Experiment 11

This experiment illustrates a synthesis of N,N-bis(m-carboxybenzyl)glycine:

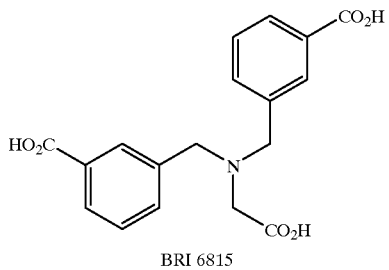

BRI 6815

Step 1: m-Cyanobenzyl bromide (2.35 g, 12.0 mmol) was slowly added to a solution of glycine methyl ester hydrochloride (0.63 g, 5.0 mmol), NaHCO$_3$ (1.4 g, 17.0 mmol) and NaI (0.37 g, 2.4 mmol) in DMSO (5 mL) and THF (20 mL). The reaction was heated to reflux for 2 hours, cooled to room temperature and diluted with EtOAc (50 ml) and water (40 mL). The organic phase was washed with water (3×40 mL), saturated aqueous NaCl (40 mL), dried (Na$_2$SO$_4$), filtered and concentrated in vacuo to give N,N-Bis(m-cyanobenzyl)glycine methyl ester as a colorless oil of sufficient purity for subsequent reactions. Additional purification can be achieved by extraction into dilute aqueous acid, basification and extraction in an organic solvent. $^1$H NMR (200 MHz, CDCl$_3$): δ3.39, s, 2H; 3.71, s, 3H; 3.86, s, 4H; 7.39–7.73, m, 10H.

Step 2: The above nitrile (1.5 g, 5.02 mmol) was hydrolyzed according to the method described in Example 4, step 2 to give N,N-bis(m-carboxybenzyl)glycine (sulfate salt) as an off-white solid. MS (APCI) m/z 342 (M$^+$–1, 100%). $^{13}$C NMR (50 MHz, $d_4$-MeOH): δ53.8, 59.0, 130.2, 131.5, 132.7, 132.8, 134.2, 136.1, 169.1, 170.7.

Experiment 12

This experiment illustrates a synthesis of (3R,4R)-1,3-bis-(p-methoxybenzyl)-4,5-bis(m-phosphonophenyl)-imidazolid-2-one:

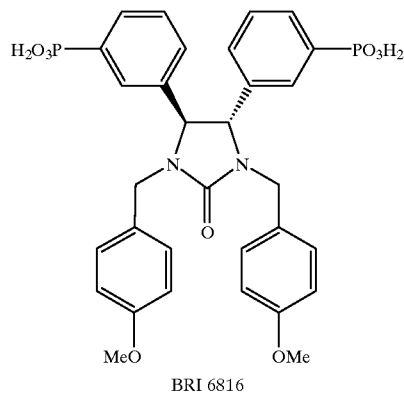

BRI 6816

Step 1: p-Methoxybenzylamine (7.42 g, 54 mmol) in CH$_2$Cl$_2$ (100 mL) containing anhydrous MgSO$_4$ was treated with m-bromobenzaldehyde (10.0 g, 54 mmol) at 0° C. The reaction was allowed to stir at room temperature for 16 hours, filtered and concentrated in vacuo to give N-p-methoxybenzyl imine of m-bromobenzaldehyde as a colorless oil. $^1$H NMR (200 MHz, CDCl$_3$): δ3.82, s, 3H; 4.78, s, 2H; 6.92, d, J=7.5 Hz, 2H; 7.16, d, J=7.5 Hz, 2H; 7.52–7.60, m, 1H; 7.62– 7.72, m, 1H; 7.98, m, 1H; 8.29, m, 1H.

Step 2: 1,2-Dibromoethane (0.5 mL) was added to zinc (1.31 g, 20.0 mmol) in CH$_3$CN (5 mL) and the mixture heated to reflux for 1 minute. Once the reaction had cooled to rt, TMSCl (1 mL) was added and the reaction stirred at room temperature for 1 hour. The above imine (6.08 g, 20 mmol) in CH$_3$CN (20 mL) was added in one portion, followed by TMSCl (3.8 mL) over 30 mins. The reaction was then stirred for 4 hours at 35–40° C. The reaction was quenched with aqueous NH$_4$OH (6 mL) and saturated aqueous NH$_4$Cl (14 mL) and filtered. The aqueous phase was separated and the aqueous phase extracted with Et$_2$O (50 mL). The combined organic extracts were dried (Na$_2$SO$_4$), filtered and concentrated in vacuo to give an orange oil. Column chromatography (SiO$_2$, 25% Et$_2$O in petroleum ether) gave (1R,2R)-N,N'-(p-methoxybenzyl)-1,2-(m-bromophenyl)ethane-1,2-diamine as a colorless oil. $^{13}$C NMR (50 MHz, CDCl$_3$): δ50.5, 55.3, 67.4, 113.8, 122.4, 126.7, 129.2, 129.6, 130.3, 130.7, 132.1, 143.4, 158.7.

Step 3: N,N'-Disuccinimidyl carbonate (160 mg, 0.64 mmol) was added to a solution of the above diamine (260 mg, 0.43 mmol) in CH$_3$CN (10 mL). The reaction was heated to reflux for 2 hours. A further charge of N,N'-disuccinimidyl carbonate (160 mg, 0.64 mmol) was added and the reaction heated to reflux for a further 2 hours. The reaction was concentrated and partitioned between EtOAc (40 mL) and aqueous HCl (1 M, 40 mL). The organic phase was washed with saturated aqueous NaHCO$_3$ (40 mL), saturated NaCl (40 mL), dried (Na$_2$SO$_4$), filtered and concentrated in vacuo to give an orange oil. Column chromatography (SiO$_2$, 25% Et$_2$O in petroleum ether→EtOAc) gave (3R,4R)-1,3-bis-(p-methoxybenzyl)-4,5-bis(m-bromophenyl)-imidazolid-2-one as a white solid. $^{13}$C NMR (50 MHz, CDCl$_3$): δ45.3, 55.2, 65.0, 111.4, 123.1, 125.9, 128.1, 129.8, 130.2, 130.5, 131.7, 140.7, 159.1, 159.9.

Step 4: The above urea (200 mg, 0.31 mmol) was treated with diethyl phosphite under the conditions described in Example 3, step 1 to give (3R,4R)-1,3-bis-(p-methoxybenzyl)-4,5-bis[m-(diethoxyphosphono)phenyl]-imidazolid-2-one as a colorless oil. MS (APCI) m/z 750 (M$^+$+1, 100%). $^{31}$P NMR (81 MHz, proton decoupled, CDCl$_3$): δ+18.4.

Step 5: The above phosphonate (340 mg, 0.45 mmol) was treated with trimethylsilyl bromide under the conditions described in Example 3, step 2 to give (3R,4R)-1,3-bis-(p-methoxybenzyl)-4,5-bis(m-phosphonophenyl)-imidazolid-2-one as an off white solid. $^{31}$P NMR (81 MHz, proton decoupled, CDCl$_3$): δ+11.5.

Experiment 13

This experiment illustrates a synthesis of 6-amino-4-(4'-pyridyl)-2-(1H)-pyridone:

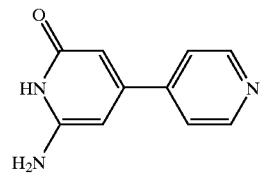

BRI 6825

Step 1: Reaction of 4,4'-bipyridine with NaNH$_2$ according to JOC, 1997, 62, 2774 gave, in addition to the reported 2,2'-diamino-4,4'-bipyridine, the previously unreported 2-amino-4,4'-bipyridine. $^{13}$C NMR (50 MHz, d$_6$-DMSO): δ105.0, 109.5, 120.9, 145.4, 148.9, 150.3, 160.5.

Step 2: The above amino-pyridine (1.5 g, 10.5 mmol) was dissolved in acetic anhydride (20 mL) and heated to 60° C. for 3 hours. The reaction was cooled to room temperature and filtered. The solid was washed with Et$_2$O (2×50 mL) and dried in vacuo to give 2-(acetylamino)-4-(4'-pyridyl)-pyridine as a light brown solid. $^1$H NMR (200 MHz, d$_6$-DMSO): δ2.12, s, 3H; 7.40–7.58, m, 1H; 7.60–7.83, m, 2H; 8.30–8.58, m, 2H; 8.62–8.88, m, 2H.

Step 3: The above pyridine (0.9 g, 4.2 mmol) was dissolved in CH$_2$Cl$_2$ (50 mL) and treated with m-chloroperbenzoic acid (4.86 g, 60% wt) and the reaction heated to reflux for 16 hours. The reaction was cooled to rt, filtered and the precipitate was washed with Et$_2$O (2×50 mL). The precipitate was added to acetic anhydride (25 mL) and heated to reflux for 4 hours, cooled to room temperature and the precipitate collected. The precipitate was added to methanol (5 mL) and treated with Na$_2$CO$_3$ (50 mg) and heated to reflux for 5 hours. The reaction was cooled to rt, filtered and the filtrate concentrated in vacuo. Trituration with Et$_2$O gave 6-amino-4-(4'-pyridyl)-2-(1H)-pyridone as a yellow solid. MS (CI) m/z 188 (M$^+$+1, 100%). $^1$H NMR (200 MHz, d$_4$-MeOH): δ5.83, d, J=1 Hz, 1H, 5.90, d, J=1 Hz, 1H; 7.67, d, J=7 Hz, 2H; 8.16, d, J=7 Hz, 2H.

Experiment 14

This experiment illustrates Fc receptor modulating activity of some of the compounds of the present invention.

Figure 5A:
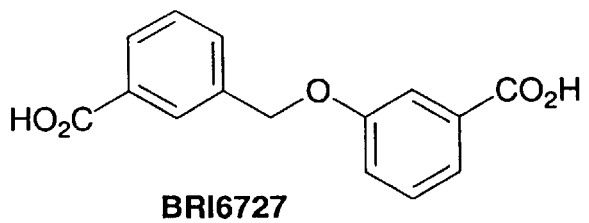
FIGS. 5A–5G show some of the Fc receptor modulating compounds including those corresponding to Fc receptor modulating activities shown in FIGS. 6–9.
Figure 5A:
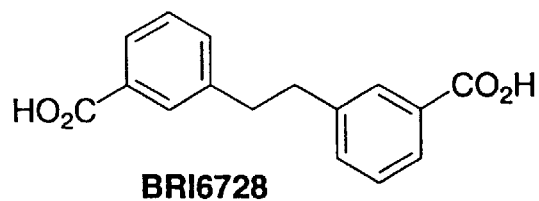
Figure 5A:
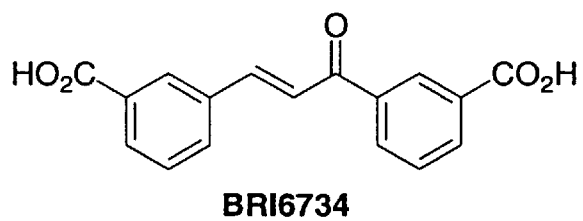
Figure 5A:
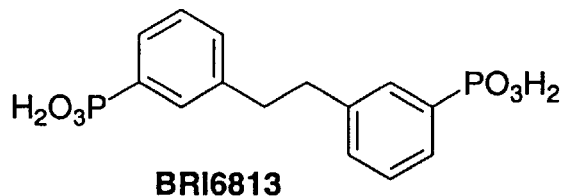
Figure 5A:
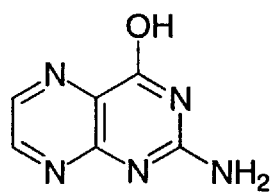
Figure 5B:
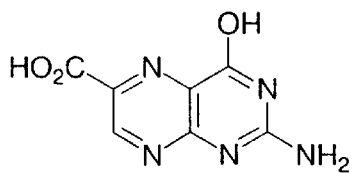
Figure 5B:
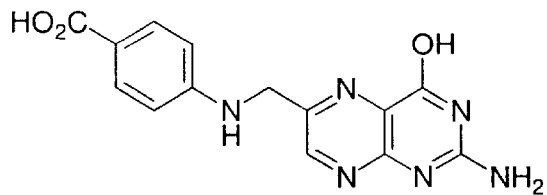
Figure 5B:
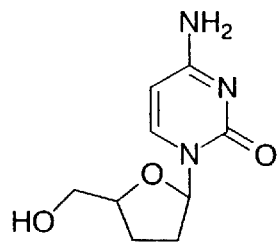
Figure 5B:
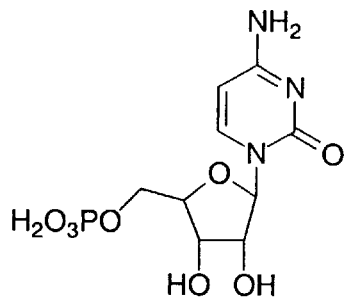
Figure 5B:
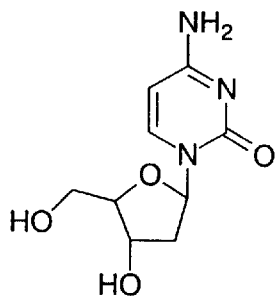
Figure 5C:
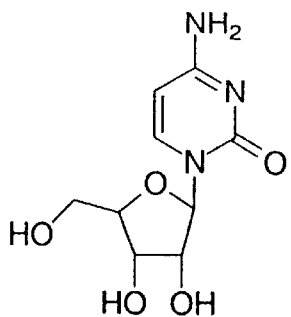
Figure 5C:
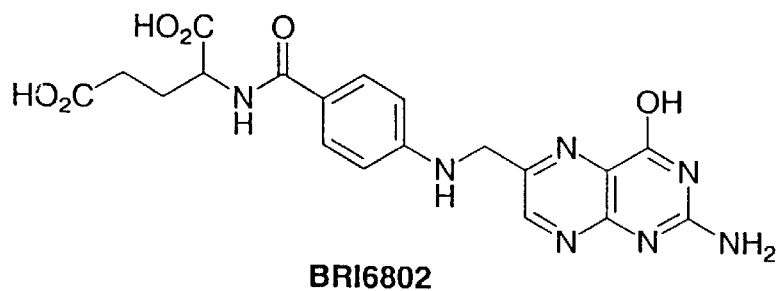
Figure 5C:
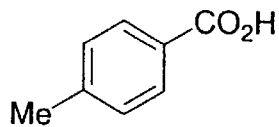
Figure 5C:
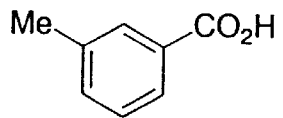
Figure 5C:
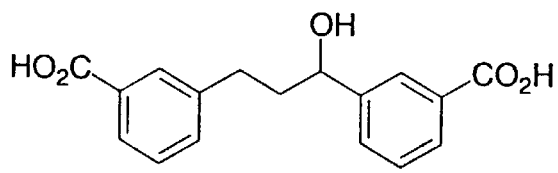
Figure 5D:
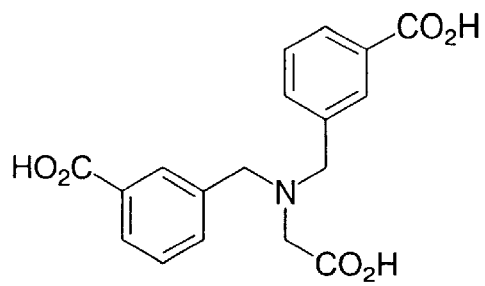
Figure 5D:
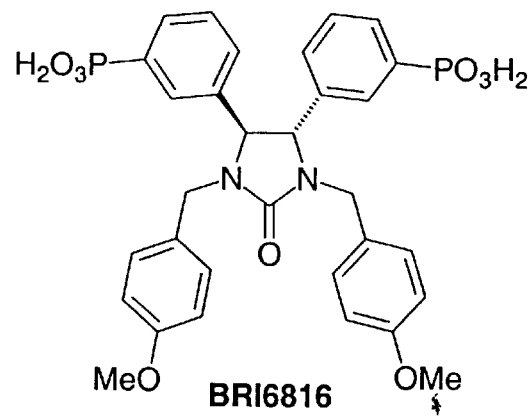
Figure 5D:
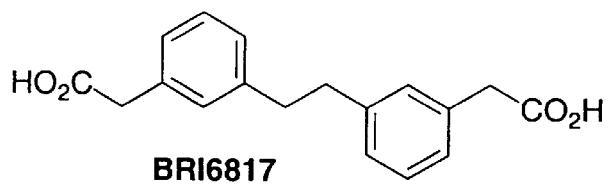
Figure 5D:
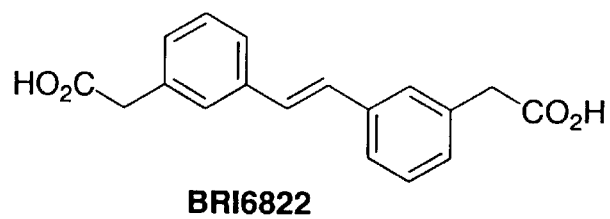
Figure 5D:
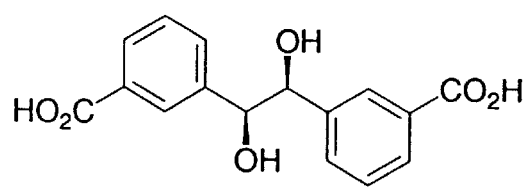
Figure 5E:
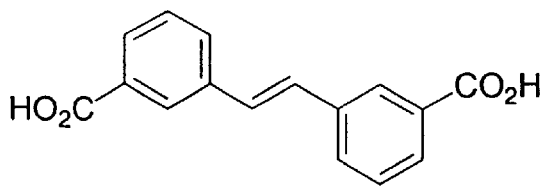
Figure 5E:
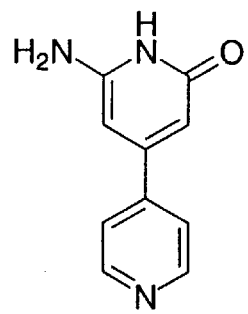
Figure 5E:
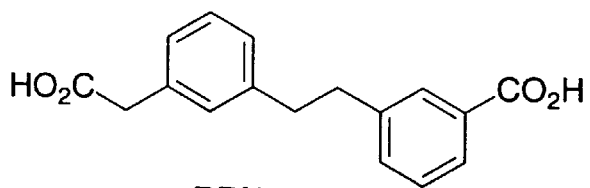
Figure 5E:
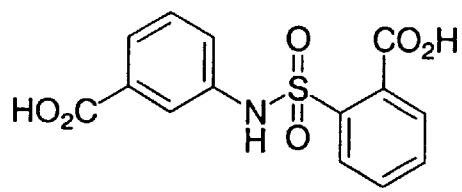
Figure 5E:
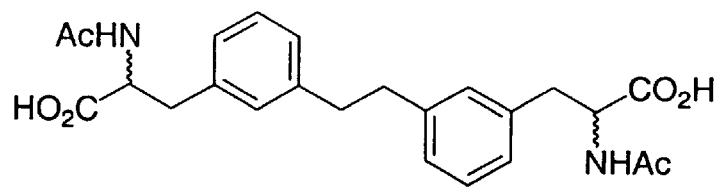
Figure 5F:
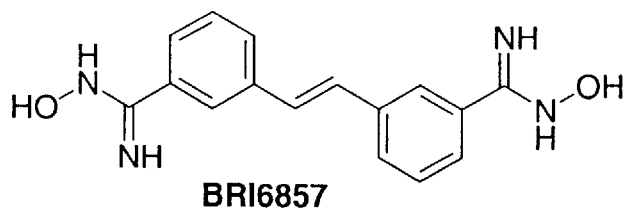
Figure 5F:
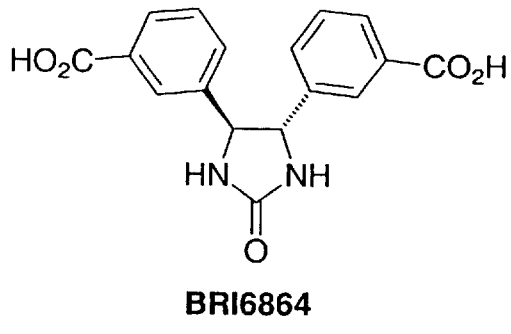
Figure 5F:
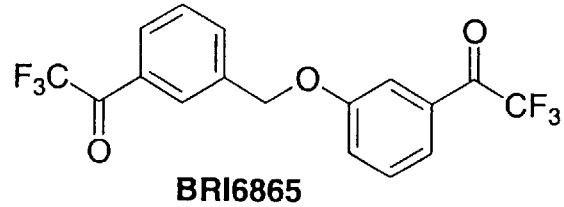
Figure 5F:
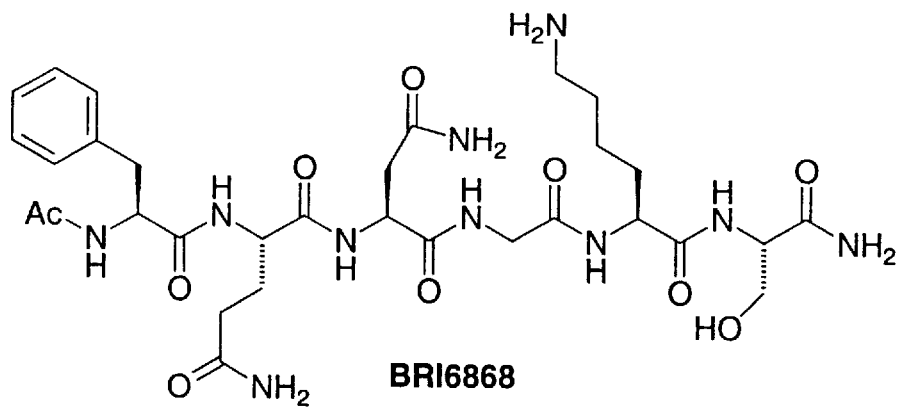
Figure 5F:
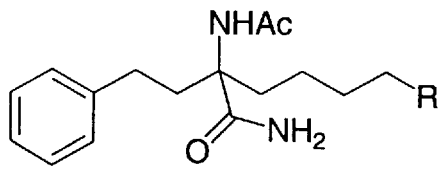
Figure 5G:
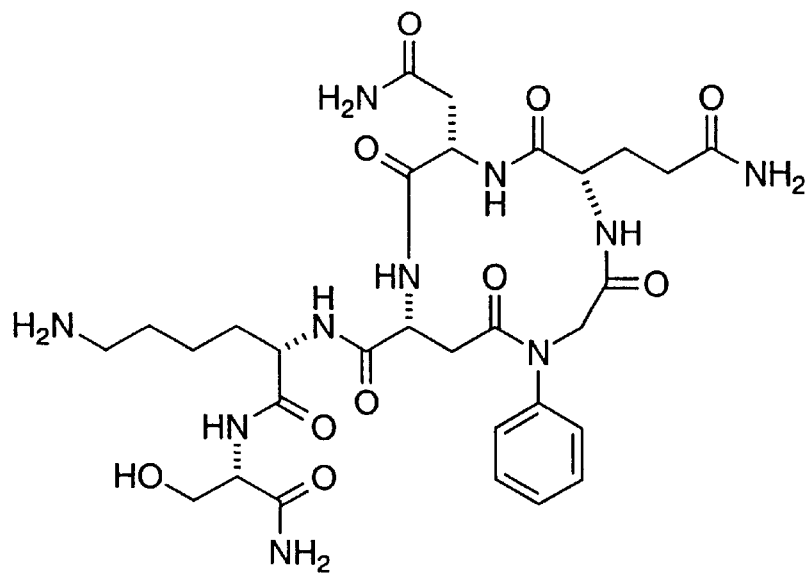
Figure 5G:
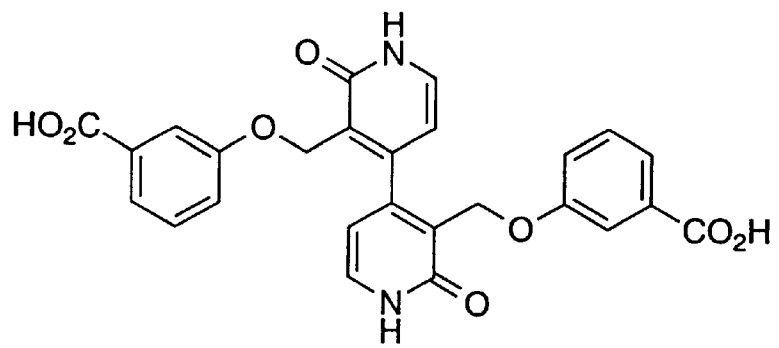

The interaction between recombinant soluble FcγRIIa and human immunoglobulin in the presence of small compounds shown in FIGS. 5A and 5B were investigated using a BIAcore 2000 biosensor (Pharmacia Biotech, Uppsala, Sweden) at 22° C. in Hepes buffered saline [HBS: 10 mM Hepes (pH 7.4), 150 mM NaCl, 3.4 mM EDTA, 0.005% Surfactant P20 (Pharmacia)]. Monomeric human IgG1, IgG3, and IgE (50 μg/mL) (non-specific binding control) were covalently coupled to the carboxymethylated dextran surface of the CM-5 sensor-chip (BIAcore, Uppsala, Sweden) using the amine coupling protocol (BIAcore, Uppsala, Sweden). An additional channel was chemically treated using the coupling protocol. Recombinant soluble FcγRIIa was used as a concentration of 125 μg/mL which was equivalent to 50% binding capacity. Recombinant soluble FcγRIIa was preincubated with each of the compounds at room temperature for 30 minutes before being injected over the sensor-chip surface for 1 minute at 10 μL/min followed by a 3 minute dissociation phase. All surfaces were regenerated with 50 mM diethylamine (about pH 11.5), 1 M NaCl between each of the compounds being analyzed. The maximum response for each interaction was measured. Non-specific binding responses (IgE channel) were subtracted from binding to IgG1 and IgG3. Measurements were corrected for differences in buffer composition between the compounds and receptor.

Figure 6:
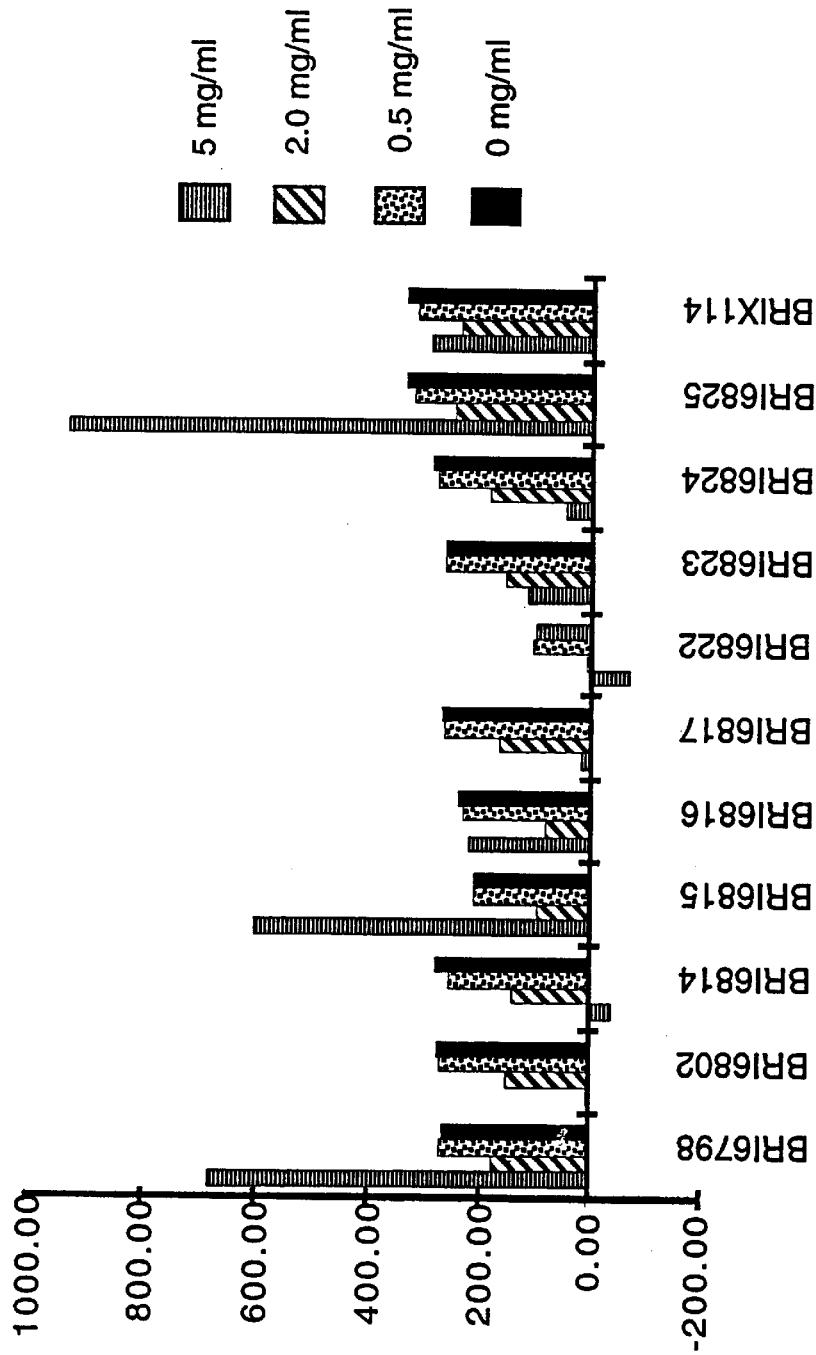
FIG. 6 shows modulating activity of FcγRIIa binding to human IgG1 by some of the compounds in FIGS. 5A and 5B.
Figure 7:
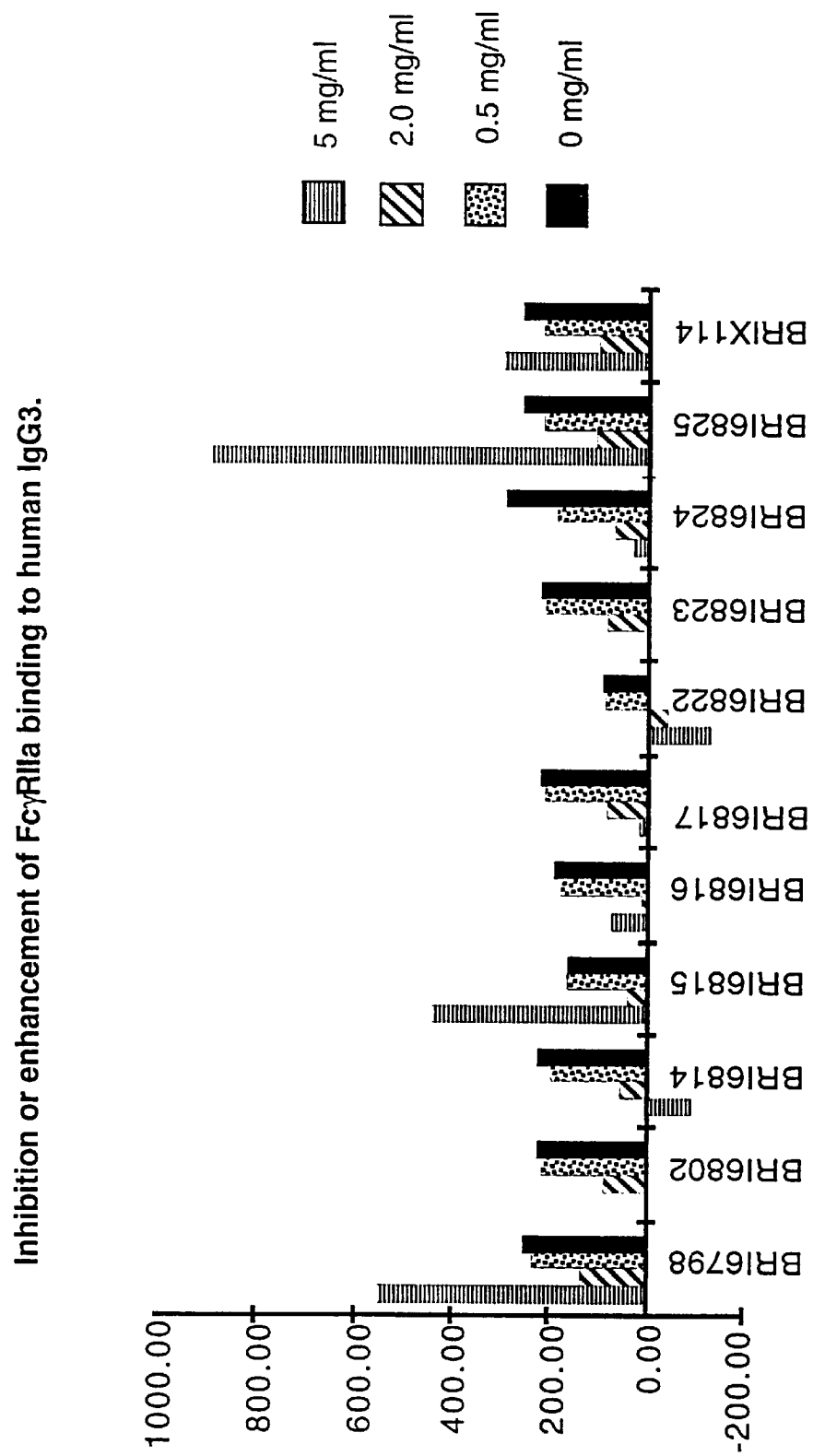
FIG. 7 shows modulating activity of FcγRIIa binding to human IgG3 by some of the compounds in FIGS. 5A and 5B.
Figure 8:
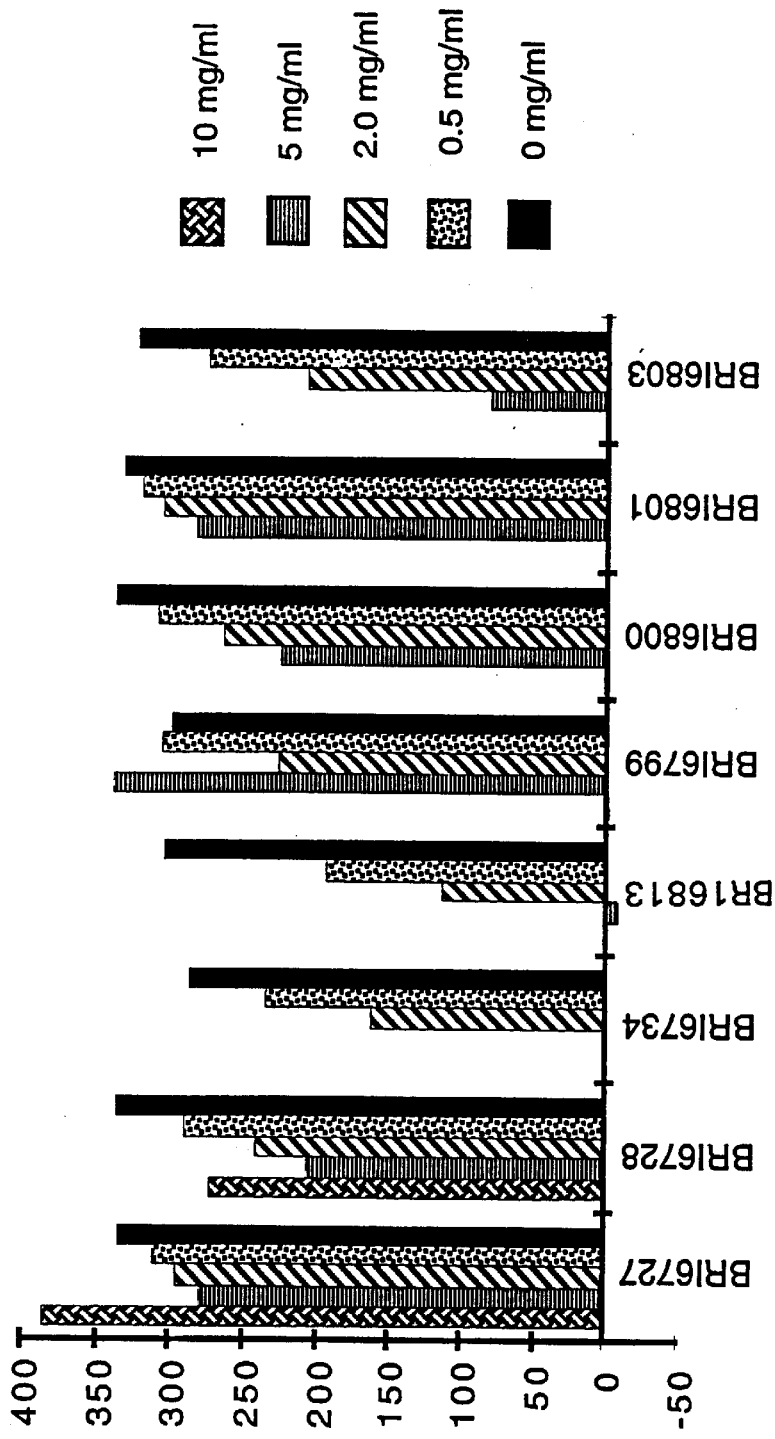
FIG. 8 shows modulating activity of FcγRIIa binding to human IgG1 by some of the compounds in FIG. 5A and 5B.
Figure 9:
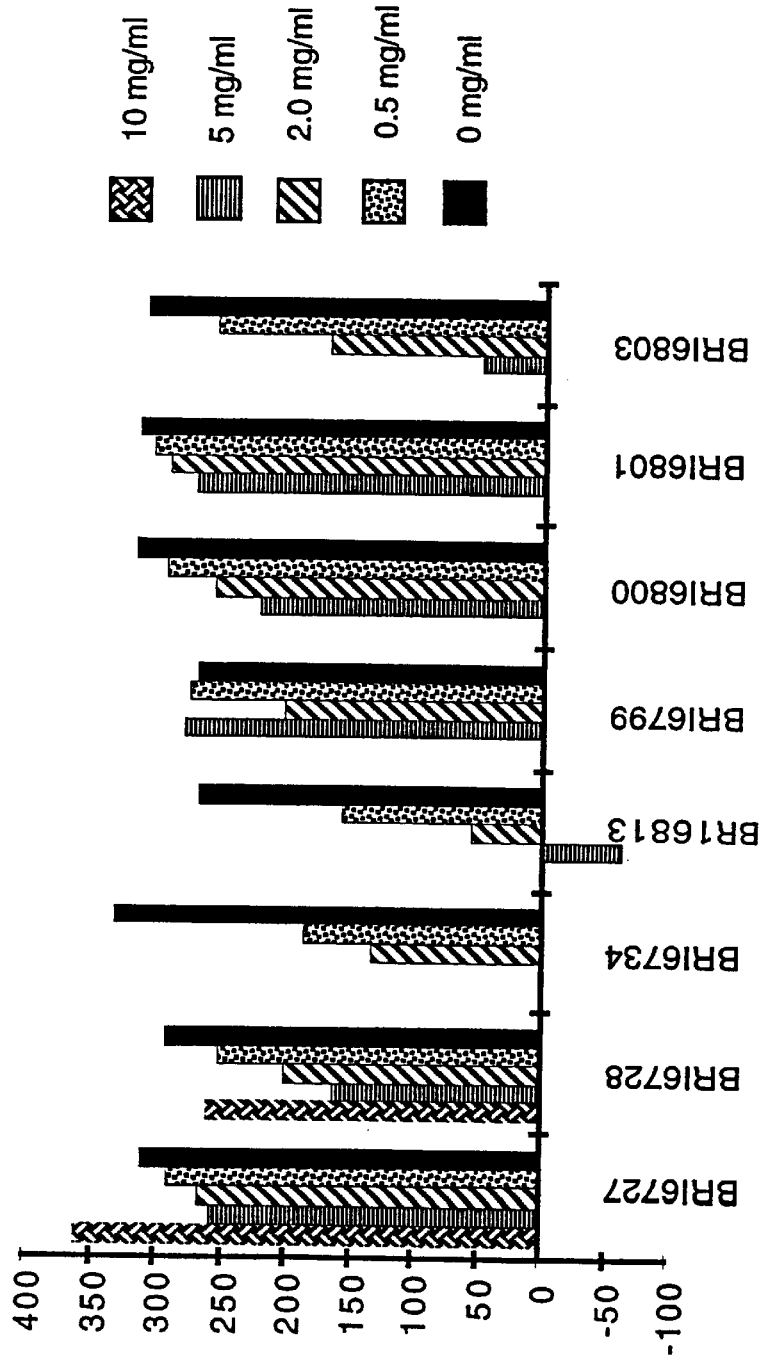
FIG. 9 shows modulating activity of FcγRIIa binding to human IgG3 by some of the compounds in FIGS. 5A and 5B.

Using the sensitivity of surface plasmon resonance the interaction of IgG1 (FIGS. 6 and 8) and IgG3 (FIGS. 7 and 9) with soluble FcγRIIa in the presence of compounds was measured. Compounds BRI6728, BRI6734, BRI6813, BRI6800, BRI6801, BRI6802, BRI6803, BRI6814, BRI6817, BRI6822, BRI6823, and BRI6824 all inhibited the interaction of soluble FcγRIIa with IgG1 (FIGS. 6 and 8). At concentrations of 5 mg/mL, compounds BRI6798, BRI6799, BRI6815, and BRI6825 enhanced the interaction between soluble FcγRIIa with IgG1 (FIGS. 6 and 8). Compounds BRI6728, BRI6734, BRI6813, BRI6800, BRI6801, BRI6802, BRI6803, BRI6814, BRI6816, BRI6817, BRI6822, BRI6823 and BRI6824 inhibited the interaction of soluble FcγRIIa with IgG3 (FIGS. 7 and 9). Compounds BRI6727, BRI6798, BRI6815 and BRI6825 all enhanced the interaction between soluble FcγRIIa with IgG3 at concentration of about 5 mg/mL and 10 mg/mL.

Experiment 15

This experiment illustrates a synthesis of N-(3'-carboxyphenyl)-2-(carboxybenzene)sulfonamide:

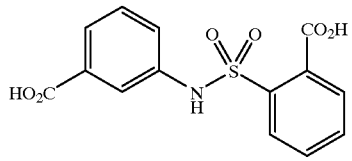

BRI 6855

Step 1: Methyl 2-(chlorosulfonyl)-benzoate (2.25 g, 8.73 mmol) in methylene chloride (20 mL) was added dropwise to a solution of ethyl 3-aminobenzoate (1.44 g, 8.73 mmol) and triethylamine (1.21 mL, 8.73 mmol) in methylene chloride (10 mL) at 0° C. The reaction was allowed to warm to room temperature and stirred overnight. The reaction mixture was washed with water (20 mL), aqueous HCl (1 M, 20 mL) and aqueous NaOH (1 M, 20 mL), dried (MgSO$_4$), filtered and concentrated in vacuo to give an orange oil. Trituration with ethyl ether gave N-(3'-carboethoxyphenyl)-2-(carbomethoxy)benzenesulfonamide as white solid. $^1$H NMR (200 MHz, CDCl$_3$): δ1.31, t, J=6.0 Hz, 3H; 4.00, s, 3H; 4.29, q, J=6.0 Hz, 2H; 7.23–7.61, m, 5H; 7.66–7.92, m, 3H; 8.26, br s , 1H.

Step 2: The above diester (1.0 g, 2.75 mmol) was hydrolyzed using the procedure described in Example 6, step 2 to provide N-(3'-carboxyphenyl)-2-(carboxybenzene)sulfonamide as a white solid. MS (CI) m/z 320 (M$^+$–1, 100%). $^{13}$C NMR (50 MHz, d$_6$-DMSO): δ168.0, 166.3, 137.3, 135.8, 133.4, 132.6, 131.3, 130.1, 129.0, 128.8, 128.0, 124.5, 123.8 and 120.5.

Experiment 16

This experiment illustrates a synthesis of trans-3,3'-bis-(N-hydroxyamidino)stilbene:

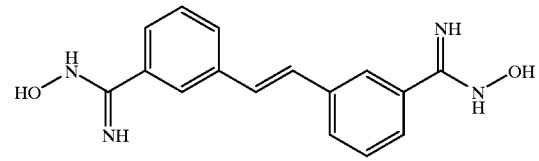

BRI 6857

Step 1: Trans-3,3'dicyanostilbene was prepared from 3-bromobenzonitrile using the method of Example 6, Step 1. MS(CI) m/z 230 (M$^+$, 100%).

Step 2. Trans-3,3'-dicyanostilbene (1.5 g, 6.52 mmol), hydroxylamine hydrochloride (3.26 g, 50 mmol) and Na$_2$CO$_3$ (3.04 g, 30 mmol) in EtOH (40 mL) and water (15 mL) was heated to reflux for 3 h. The reaction was cooled to room temperature and the ethanol was removed in vacuo. The remaining solution was extracted with EtOAc (2×50 mL) and the combined organic extracts was washed with aqueous HCl (1 M, 2×20 mL). The combined aqueous extracts were made basic and extracted with EtOAc (3×50 mL). The combined organic extracts were dried (MgSO$_4$), filtered and concentrated in vacuo to give a colorless solid. MS (CI) m/z 297 (M$^+$+1, 100%). $^{13}$C NMR (50 MHz, d$_6$-DMSO): δ123.3, 124.8, 127.1, 128.6, 133.8, 136.8 and 150.7.

Experiment 17

This experiment illustrates a synthesis of (d,l)-and meso-2-acetylamino-3-(3-{2-[3-(2-acetylamino-2-carboxyethyl)phenyl]ethyl}-phenyl)propionic acid:

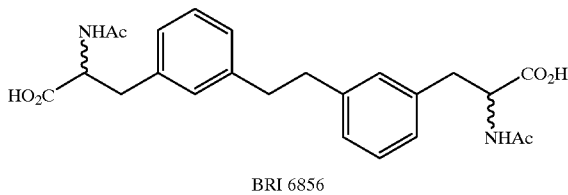

BRI 6856

Step 1: 3-Bromobenzaldehyde (23.7 g, 128.2 mmol), N-acetyl glycine (10.0 g, 85.5 mmol) and sodium acetate (5.26 g, 64.1 mmol) in acetic anhydride (60 mL) was heated to reflux for 1 h. The reaction was cooled to room temperature and water (100 mL) was added. The resulting suspension was filtered and the solid was washed with water (2×50 mL). The remaining solid was dissolved in methylene chloride (100 mL), dried (MgSO$_4$), filtered and concentrated in vacuo to give a yellow solid. The solid was suspended in dry MeOH (200 mL) and heated to reflux for 9 h. The reaction mixture was concentrated in vacuo to give a yellow solid. Recrystallization from EtOAc and petroleum ether gave methyl m-bromo-α-acetamidocinnamate as a yellow solid. MS (CI) m/z 298 (M$^+$+1 (Br=79), 100%), 300 (M$^+$+1 (Br=81), 100%). $^{13}$C NMR (50 MHz, d$_6$-DMSO): δ23.3, 52.8, 122.5, 125.0, 128.06, 130.0, 130.2, 132.2, 132.3, 135.9, 165.4 and 168.8.

Step 2: Trans-methyl 2-acetylamino-3-(3-{2-[3-trans-(trans-2-acetylamino-2-carbomethoxyethenyl)phenyl]ethenyl}phenyl)prop-2-enoate was prepared from the above compound using the method of Example 6, step 1. MS (CI) m/z 461 (M$^+$–1, 100%).

Step 3: The compound from step 2 (380 mg, 0.82 mmol) and Pd/C (300 mg, 10%) in MeOH (20 mL) was stirred under a hydrogen atmosphere at room temperature for 16 h. The reaction was filtered and concentrated in vacuo to give (d,l)- and meso-methyl 2-acetylamino-3-(3-{2-[3-(2-acetylamino-2-carbomethoxy-ethyl)phenyl]-ethyl}-phenyl)-propanoate as a clear viscous oil which was used without further purification.

Step 4: The compound from step 3 (280 mg, 0.60 mmol) was hydrolyzed using the procedure described in Example 6, step 2 to give (d,l) -and meso-2-acetylamino-3-(3-{2-[3-(2-acetylamino-2-carboxyethyl)phenyl]ethyl}-phenyl) propionic acid as a clear viscous oil. MS (CI) m/z 440 (M$^+$–1, 100%).

Experiment 18

This experiment illustrates a synthesis of (3R,4R)-4,5-bis(m-carboxyphenyl)imidazolid-2-one:

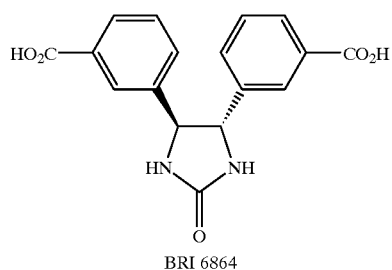

BRI 6864

Step 1: Methanesulfonyl chloride (1.01 mL, 13.1 mmol) was added dropwise to a solution of (R,R)-1,2-bis-[3-(carbomethoxy)phenyl]ethane-1,2-diol (Example 7, step 1) (1.5 g, 4.54 mmol) in pyridine (10 mL) at 0° C. The reaction was allowed to warm to room temperature and stirred overnight. The reaction was diluted with water (30 mL) and 30 mL of methylene chloride and the aqueous phase was extracted with 2×10 mL of methylene chloride. The combined organic extracts were washed with 2×20 mL of 1 M aqueous HCl, 20 mL of aqueous sodium bicarbonate, dried over magnesium sulfate, filtered and concentrated in vacuo to give di-methanesulfonate of (R,R)-1,2-bis-[3-(carbomethoxy)phenyl]ethane-1,2-diol as a yellow viscous oil.

Step 2: A solution of the above mesylate (505 mg, 1.0 mmol) and NaN$_3$ (150 mg, 2.31 mmol) in 6 mL of DMF was heated to 90° C. for 17 h. The reaction mixture was cooled to rt, diluted with 50 mL of diethyl ether and washed with 3×50 mL of water. The organic phase was dried over MgSO$_4$, filtered and concentrated in vacuo to give (R,R)-1, 2-bis-3-(carbomethoxy)phenyl]-1,2-diazo-ethane as a yellow viscous oil. $^1$H NMR (200 MHz, CDCl$_3$): δ3.93, s, 3H; 4.73, s, 1H; 7.17–7.39, m, 2H; 7.78–8.01, m, 2H.

Step 3: The above diazide (611 mg, 1.61 mmol) and Pd on carbon (10%, 50 mg) in methanol was treated with concentrated aqueous HCl (3.86 μL, 3.86 mmol). The reaction was placed under a hydrogen atmosphere and stirred at room temperature for 30 h. The reaction was filtered through celite and concentrated to give the hydrochloride salt of (R,R)-1, 2-bis-[3-(carbomethoxy)phenyl]-1,2-diamino-ethane. MS (CI) m/z 329 (M$^+$+1 for the free amine, 70%), 312 (100%).

Step 4: The above diamine (in free base form) (280 mg, 0.85 mmol) in 5 mL of acetonitrile was treated with DMAP (104 mg, 0.85 mmol) a solution of di-tert-butyl dicarbonate (204 mg, 0.94 mmol) in 1 mL of acetonitrile at rt. The reaction was stirred for 25 min at room temperature and partitioned between 50 mL of ether and 50 mL of 1 M HCl. The organic phase was separated, dried over sodium sulfate, filtered and concentrated in vacuo. Column chromatography gave (3R,4R)-4,5-bis-(m-carbomethoxyphenyl)imidazolid-2-one as a white solid. MS (APCI) m/z 355 (M$^+$+1, 100%). $^1$H NMR (200 MHz, d$_6$-DMSO): δ3.86, s, 6H; 4.57, s, 2H; 7.16, br s, 2H; 7.46–7.61, m, 4H; 7.88–8.00, m, 4H.

Step 5: The above diester (68 mg, 0.19 mmol) was hydrolyzed using the procedure described in Example 6, step 2 to give (3R,4R)-4,5-bis(m-carboxyphenyl) imidazolid-2-one as a white solid. MS (electrospray) m/z 327 (M$^+$+1, 100%). $^{13}$C NMR (50 MHz, d$_6$-DMSO): δ64.3, 127.4, 129.1, 129.3, 131.1, 131.4, 142.1, 162.5, 167.3.

Experiment 19

This experiment illustrates a synthesis of 3-([3'-(1"-oxo-2",2",2"-trifluoroethyl)phenoxy]methyl)phenyl trifluoromethyl ketone:

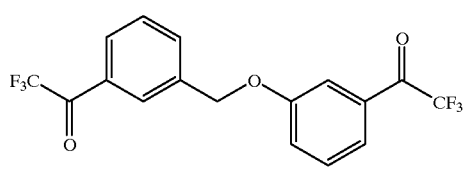

BRI 6865

Tert-butyl lithium (1.6 mL, 1.7 M in pentane, 2.72 mmol) was added dropwise to a solution of 3-[(m-bromophenyl)methoxy]bromo-benzene (Example 2, step 1) (233 mg, 0.68 mmol) in 6 mL of THF at –78° C. After 20 min at this temperature, the solution was added dropwise to a solution of ethyl trifluoroacetate (0.35 mL, 2.94 mL) in 5 mL of THF at −78° C. The reaction mixture was stirred for 16 h during which time the reaction mixture reached rt. The reaction mixture was partitioned between 20 mL of 1 M HCl and 50 mL of ether. The organic phase was separated, dried over sodium sulfate, filtered and concentrated in vacuo to provide 3-([3'-(1"-oxo-2",2",22"-trifluoroethyl)phenoxy]methyl) phenyl trifluoromethyl ketone as a colorless oil. MS (CI) m/z 377 (M$^+$+1, 100%), $^{19}$F NMR (188 MHz, CDCl$_3$): δ−71.76 and −71.90.

Experiment 20

This experiment illustrates a synthesis of Ac-Phe-Gln-Asn-Gly-Lys-Ser-NH$_2$:

gave tert-butyl N-[(4S)-3-benzyloxycarbonyl-5-oxo-oxazolidin-4-yl-acetyl]-N-phenylglycinate as a white foam. MS (APCI) m/z 467 (M$^+$−1, 100%).

Step 2: Aqueous NaOH (3 mL, 1 M, 3 mmol) was added dropwise to a solution of the above dipeptide (570 mg, 1.22 mmol) in methanol (20 mL) at 0° C. The reaction was allowed to warm to room temperature and monitored by TLC. The reaction was concentrated and partitioned between Et$_2$O (30 mL) and citric acid (10%, 30 mL) at 0° C. The aqueous phase was extracted with Et$_2$O (3×30 mL), and the combined organic extracts were dried (MgSO$_4$), filtered and concentrated in vacuo to give a white solid. Column

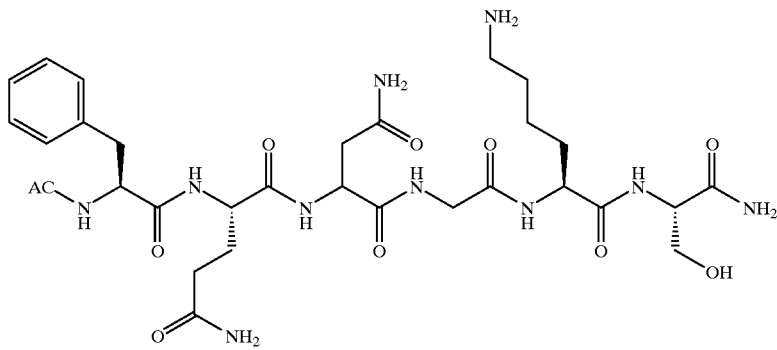

BRI 6868

The peptide was assembled using solid phase peptide synthesis techniques. N-Acylation and cleavage from the resin gave the title compound as a while sold. HPLC and MS analysis confirmed the purity and identity of this material.

Experiment 21

This experiment illustrates a synthesis of Cyclo-[N-Phenylglycine-Gln-Asn-(D)-Asp]-Lys-Ser-NH$_2$:

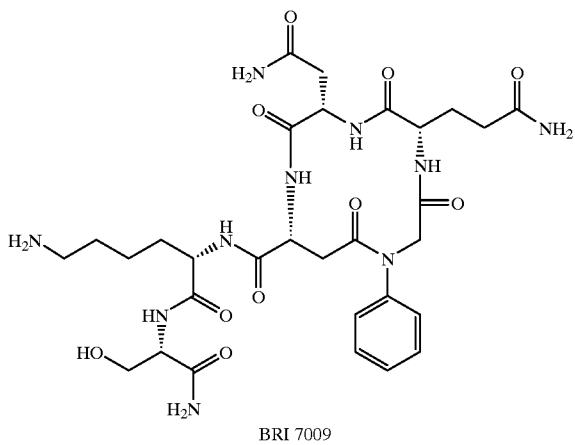

BRI 7009

Step 1: N-[(4S)-3-benzyloxycarbonyl-5-oxo-oxazolidin-4-yl-acetyl chloride (3.00 g, 10 mmol) in dichloromethane (20 mL) was added dropwise to a solution of tert-butyl-N-phenylglycinate (2.3 mg, 11 mmol) in pyridine (10 mL) at 0° C. The reaction was allowed to warm to room temperature and stirred overnight. The reaction was diluted with H$_2$O (100 mL) and EtOAc (150 mL). The organic phase was separated and washed successively with citric acid (10%, 2×100 mL) and brine (100 mL), dried (MgSO$_4$), filtered and concentrated in vacuo to give a yellow viscous oil. Column chromatography (SiO$_2$, 20–50% EtOAc in petroleum ether)

chromatography (SiO$_2$, 2–5%, MeOH in dichloromethane) gave tert-butyl N-[(2S)-N-benzyloxycarbonyl-aspartyl]-β-N-phenylglycinate as a white solid. MS (APCI) m/z 456 (M$^+$+1, 90%).

Step 3: The above compound (1.35 g, 2.96 mol) in MeOH (40 mL) containing palladium on carbon (10%, 500 mg) was placed under an atmosphere of hydrogen and stirred at room temperature for 16 hours. The reaction was filtered and concentrated in vacuo to give tert-butyl N-[(2S)-asparty])-β-N-phenylglycinate as an off white solid.

Step 4: The above compound (890 mg, 2.76 mmol), Fmoc-O-Su, i.e., N-(9-fluorenylmethoxycarbonyloxy) succinimide, (932 mg, 2.76 mmol), Na$_2$CO$_3$ (880 mg, 8.29 mmol) in dioxane (15 mL) and H$_2$O (15 mL) was stirred at room temperature for 16 hours. The reaction was diluted with Et$_2$O (100 mL) and H$_2$O (100 mL). The organic layer was separated and extracted with aqueous Na$_2$CO$_3$ (5%, 3×100 mL). The combined aqueous extracts were acidified with 10% aqueous citric acid and extracted with EtOAc (3×100 mL). The organic extracts were combined, dried (MgSO$_4$), filtered and concentrated in vacuo to give tert-butyl N-[(2S)-N-Fmoc-asparty])-β-N-phenylglycinate as a white solid. $^{13}$C NMR (50 MHz, d$_6$-DMSO): δ28.0, 36.7, 47.0, 50.4, 52.4, 67.0, 67.3, 82.3, 119.9, 125.2, 125.3, 127.1, 127.7, 127.8, 128.8, 130.1, 141.2, 142.8, 143.7, 143.9, 156.1, 167.6, 171.6, 174.5.

Step 5: Solid phase amino acid synthesis using the above Fmoc protected dipeptide followed by cyclization on the resin and cleavage gave cyclo-[N-phenylglycine-Gln-Asn-(D)-Asp]-Lys-Ser-NH$_2$.

Experiment 22

This experiment illustrates a synthesis of 2-(2'-phenylethyl)-α-N-acetyl-lysine amide and its hydrochloride salt:

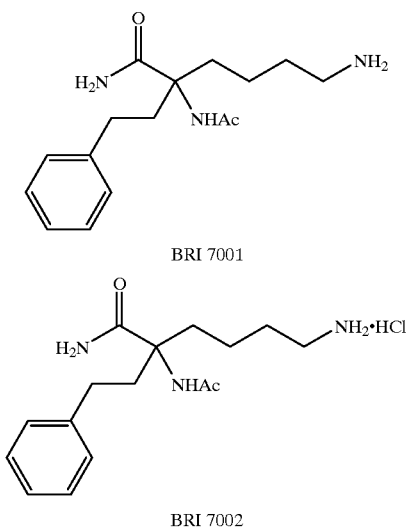

BRI 7001

BRI 7002

Step 1: To a mixture of sodium metal (138 mg, 5.98 mmol) in dry ethanol (16 mL) was added 2-cyano-4-(phenethyl)ethylbutanoate (1.0 g, 4.6 mmol) and the mixture was stirred at room temperature for 30 min. 4-Bromo-but-1-ene (0.6 mL, 6 mmol) was then added and the mixture was heated at reflux for 16 hours. The resulting suspension was cooled to room temperature, concentrated under reduced pressure and diluted with ether (100 mL) and NH$_4$Cl (100 mL of a saturated aqueous solution). The aqueous layer was separated and extracted with ether (3×50 mL). The organic layers were combinec, dried (MgSO$_4$), filtered and concentrated to give a light brown oil. Column chromatography (silica, 20% ether/petrol elution) afforded ethyl 2-cyano-2-(2'-phenethyl)-hex-5-enoate as a clear, colorless oil. $^1$H NMR (200 MHz, CDCl$_3$) δ1.35 (t, J=7.0 Hz, 3H), 1.82–2.45 (m, 6H), 2.65 (td, J=12.4 Hz and 7.0 Hz, 1H), 2.90 (td, J=12.4 Hz and 7.0 Hz, 1H), 4.24 (q, J=7.0 Hz, 2H), 5.00–5.13 (m, 2H), 5.67–5.76 (m, 1H), 7.15–7.35 (m, 5H).

Step 2: A mixture of the above olefin (0.72 g, 2.65 mmol), LiOH (10.6 mL, 1.0 M, 10.6 mmol) and THF (50 mL) was stirred at room temperature for 18 hours. The reaction mixture was diluted with ether (100 mL) and water (100 mL) and the phases separated. The aqueous layer was acidified to ca, pH 2 with 2 M aqueous HCl solution and transferred to a separating funnel containing ether (100 mL). The separated aqueous layer was extracted with ether (3×50 mL). The organic fractions were combined, dried (MgSO$_4$), filtered and concentrated under reduced pressure to afford 2-cyano-2-(2'-phenethyl)-5-hexenoic acid as a viscous, colorless oil. This material was used in the next reaction without further purification. MS (APCI) m/z 244 (M$^+$+1, 55%), 242 (M$^+$−1, 63%).

Step 3: Diphenyl phosphoryl azide (2.75 mL, 12.8 mmol) and triethylamine (1.75 mL, 12.6 mmol) were added to a solution of the above acid (2.6 g, 10.7 mmol) in toluene (35 mL). The solution was heated at 100° C. for 1 hour after which time tert-butanol (35 mL) was added. The mixture was heated at 100° C. for additional 2 hours, cooled to room temperature and concentrated under reduced pressure. The resulting yellow oil was diluted with ether (300 mL) and water (300 mL). The organic layer was separated, washed successively with citric acid (100 mL of a 5% aqueous solution), NaHCO$_3$ (100 mL of a 5% aqueous solution) and brine (100 mL), dried (MgSO$_4$), filtered and concentrated to give a yellow oil. Column chromatography (silica, 2% ethyl acetate/chloroform elution) gave 2-(N-boc-amino)-2-(2'-phenethyl)-5-hexenonitrile as a colorless oil. MS (APCI) m/z 316 (M$^+$+1, 5%), 313 (M$^+$−1, 2%). $^{13}$C NMR (50 MHz, CDCl$_3$): δ28.4, 30.5, 36.3, 38.9, 54.9, 116.3, 119.7, 126.6, 128.4, 128.8, 136.3, 140.1, 153.5.

Step 4: NaOH (9.2 mL, 1.0 M) and H$_2$O$_2$ (38 mL of a 30% (v/v) aqueous solution) were added to a solution of the above nitrile compound (523 mg, 1.93 mmol) in ethanol (20 mL) at 0° C. The reaction mixture was stirred at 0° C. for 30 min and at room temperature for 18 hours. The ethanol was removed under reduced pressure and the residue was diluted with ether (100 mL) and brine (100 mL). The aqueous layer was separated and extracted with ether (4×20 mL). The organic layers were combined, dried (MgSO$_4$), filtered and concentrated to afford 2-(N-Boc-amino)-2-(2'-phenethyl)-5-hexenamide as a colorless sticky foam. This material was used in the next reaction without further purification R$_f$0.3 (30% ethyl acetate/petrol elution). MS (APCI) m/z 333 (M$^+$+1, 5%), 233 (100%).

Step 5: Trifluoroacetic acid (2 mL) was added to a solution of the above amide (480 mg, 1.44 mmol) in dichloromethane (5 mL), and the mixture was stirred at room temperature for 35 min. The reaction mixture was concentrated to afford 2-amino-2-(2'-phenethyl)-5-hexenamide as a red-brown oil. This material was used in the next reaction without further purification. MS (APCI) m/z 233 (M$^+$+1, 100%).

Step 6: Acetic anhydride (2.5 mL) was added to a solution of the above amine (335 mg, 1.44 mmol) in pyridine (2.5 mL) and stirred at room temperature for 21 hours. The resulting red-brown reaction mixture was concentrated under reduced pressure. Column chromatography (silica, 80% ethyl acetate/petrol elution, R$_f$0.36) gave (N-acetyl-amino)-2-(2'-phenethyl)-5-hexenamide as a straw colored foam. $^{13}$C NMR (50 MHz, CDCl$_3$): δ24.2, 28.3, 30.4, 35.2, 37.8, 64.0, 115.2, 126.1, 128.4, 128.5, 137.4, 141.1, 169.4, 175.3.

Step 7: 9-BBN (4.6 mL, 0.5 M solution in THF, 2.30 mmol) was added dropwise to a solution of the above olefin (130 mg, 0.47 mmol) in dry THF (2 ml). The reaction mixture was stirred at ambient temperature for 18 hours. The mixture was cooled to 0° C. and water (0.5 mL), NaOAc (5 mL of a 5.0 M aqueous solution) and H$_2$O$_2$ (5 mL) were added successively. The resulting mixture was stirred at room temperature for 2 hours and diluted with ethyl acetate (30 mL) and brine (30 mL). The aqueous layer was separated and extracted with ethyl acetate (3×10 mL). The organic fractions were combined, dried (MgSO$_4$), filtered and concentrated under reduced pressure to give a light yellow oil. Column chromatography (silica, 5% MeOH/ethyl acetate elution, R$_f$0.4) gave 2-(N-acetyl-amino)-2-(2'-phenethyl)-6-hydroxy-hexanamide as a colorless, sticky foam. MS (APCI) m/z 293 (M$^+$+1, 35%), 291 (M$^+$−1, 35%).

Step 8: Triethylamine (0.1 mL, 0.72 mmol) and methanesulfonyl chloride (0.05 mL, 0.65 mmol) were added to a solution of the above alcohol (88 mg, 0.30 mmol) in dichloromethane (2 mL) at 0° C. The resulting mixture was stirred at ambient temperature for 19 hours and diluted with ethyl acetate (30 mL) and brine (30 mL). The aqueous layer was separated and extracted with ethyl acetate (3×10 mL) The organic layers were combined, dried (MgSO$_4$), filtered and concentrated under reduced pressure to give 2-(N-acetyl-amino)-2-(2'-phenethyl)-6-methanesulfonyloxy-hexanamide as a tan colored residue. The crude product was used in the next reaction without further purification. MS (APCI) m/z 371 (M$^+$+1, 45%), 369 (M$^{+-}$1, 5%).

Step 9: A solution of the above mesylate (110 mg, 0.30 mmol) and sodium azide (54 mg, 0.83 mmol) in dry DMF (2 mL) was heated at 60° C. to 65° C. for 19.5 hours. The orange colored suspension was cooled to room temperature, concentrated and diluted with ethyl acetate (30 mL) and brine (30 mL). The aqueous layer was separated and extracted with ethyl acetate (4×10 mL). The organic fractions were combined, dried (MgSO$_4$), filtered and concentrated to afford 2-(N-acetyl-amino)-2-(2'-phenethyl)-6-azido-hexanamide as a tan colored oil. This material was used in the next reaction without further purification. $^1$H NMR (200 MHz, CDCl$_3$): δ1.20–1.78 (m, 6H), 1.92 (s, 3H), 2.20–3.02 (m, 1H), 3.12–3.30 (m, 2H), 5.57 (s, 1H), 5.90 (s, 1H), 6.72 (s, 1H), 7.04–7.30 (m, 5H).

Step 10: A suspension of the above azide (95 mg, 0.30 mmol) and 10% Pd on C (18.4 mg) in methanol (2 mL) was hydrogenated at room temperature and atmospheric pressure for 21 hours. The black suspension was filtered through a small plug of silica-Celite which was flushed with several portions of methanol (ca. 30 mL). Concentration of the filtrate afforded a light tan colored oil. Column chromatography (silica, 10% triethylamine/methanol elution, R$_f$0.22) gave 2-(2'-phenylethyl)-α-N-acetyl-lysine amide as a clear, colorless oil. MS (APCI), m/z 292 (M$^+$+1, 100%) 290 (M$^+$–1, 30%). $^1$H NMR (200 MHz, d$_4$-MeOD): δ1.10–1.60 (m, 4H), 1.73–1.90 (m, 1H), 1.95 (s, 3H), 1.95–2.35 (m, 2H), 2.40–2.80 (m, 5H), 7.10–7.35 (m, 5H).

A small quantity of the amine was converted to the corresponding hydrochloride salt derivative by adding 0.5 M aqueous HCl solution to the amine and concentrating the mixture under reduced pressure.

Experiment 23

This experiment illustrates a synthesis of 4,4'-bis-(3-[(m-carboxyphenoxy)methyl]-2-pyridone):

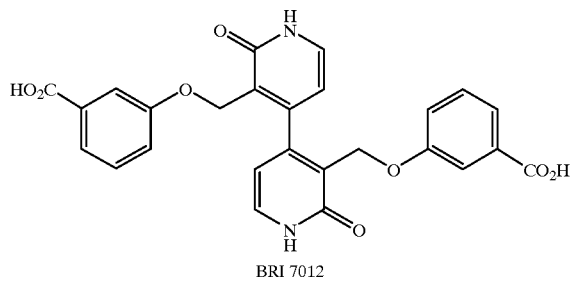

BRI 7012

Step 1: Solid NaBH$_4$ (28 mg, 0.74 mmol) was added in one portion to a solution of 3-formyl-4-iodo-2-methoxypyridine (prepared according to the method of Fang et al., *J. Org. Chem.*, 1994, 59, 6142) (98 mg, 0.37 mmol) in methanol (4 mL) at −5° C. Vigorous bubbling was observed and the yellow reaction solution turned colorless. The reaction was immediately quenched by the addition of water (2 mL) and the methanol was removed under reduced pressure. The resulting residue was diluted with ethyl acetate (20 mL) and water (20 mL). The aqueous layer was separated and extracted with ethyl acetate (3×10 mL). The organic fractions were combined, dried (MgSO$_4$), filtered and concentrated to give 3-(hydroxymethyl)-4-iodo-2-methoxypyridine as a colorless, crystalline solid. This material was used in the next reaction without further purification. R$_f$0.4 (30% ethyl acetate/petrol elution). MS (APCI, m/z 266 (M$^+$+1, 100%). $^1$H NMR (200 MHz, CDCl$_3$): δ3.98 (s, 3H), 4.80 (s, 2H), 7.34 (d, J=4.0 Hz, 1H), 7.70 (d, J=4.0 Hz, 1H).

Step 2: Methanesulfonyl chloride (0.5 mL, 6.4 mmol) was added dropwise to a solution of the above alcohol (373 mg, 1.41 mmol) and triethylamine (0.95 mL, 6.8 mmol) in dichloromethane (9.4 mL) at 0° C. The resulting mixture was stirred at ambient temperatures for 15 hours and diluted with ethyl acetate (150 mL) and brine (150 mL). The aqueous layer was separated and extracted with ethyl acetate (3×50 mL). The organic fractions were combined, dried (MgSO$_4$), filtered and concentrated under reduced pressure to afford 3-(chloromethyl)-4-iodo-2-methoxypyridine as a light tan, crystalline solid. This material was used in the next step without further purification. MS (APCI) m/z 284 (M$^+$+1, 100%). $^1$H NMR (200 MHz, CDCl$_3$): δ3.95 (s, 3H), 4.65 (s, 2H), 7.28 (d, J=4.0 Hz, 1H), 7.65 (d, J=4.0 Hz, 1H).

Step 3: The sodium salt of methyl-3-hydroxybenzoate (372 mg, 2.14 mmol) was added in one portion to a solution of the above chloride (399 mg, 1.41 mmol) in dry DMF (7 mL). The orange colored reaction mixture was stirred at room temperature for 18 hours and diluted with ethyl acetate (150 mL) and water (150 mL). The aqueous layer was separated and extracted with ethyl acetate (3×30 mL). The organic layers were combined, dried (MgSO$_4$), filtered and concentrated to give a brown oil. Column chromatography of this oil (silica, 30% ether/petrol elution, R$_f$0.35) gave 4-iodo-2-methoxy-3-{[(m-carbomethoxy)phenoxy]methyl}-pyridineas a colorless oil. MS (APCI), m/z 400 (M$^+$+1, 40%). $^1$H NMR (200 MHz, CDCl$_3$): δ3.92 (s, 3H), 3.96 (s, 3H), 5.20 (s, 2H), 7.15–7.42 (m, 3H), 7.62–7.80 (m, 3H).

Step 4: A suspension of the above iodide (0.5 g, 1.25 mmol), Pd(PPh$_3$)$_4$ (141 mg. 0.13 mmol), K$_2$CO$_3$ (518 mg, 3.76 mmol), diboron pinacol ester (159 mg, 0.63 mmol) in DMF (7.6 mL) was heated at 80° C., protected from light, for 16 hours. The dark brown reaction mixture was cooled to room temperature and diluted with ethyl acetate (150 mL) and water (150 mL). The aqueous layer was separated and extracted with ethyl acetate (3×25 mL). The organic layers were combined, dried (MgSO$_4$), filtered and concentrated under reduced pressure to give a brown oil. Column chromatography (silica, 50% ethyl acetate/petrol elution, R$_f$0.57) of this oil gave 4,4'-bis-2-methoxy-3-{[(m-carbomethoxy)phenoxy]methyl}-pyridine as a foam. MS (APCI) m/z 545 (M$^+$+1, 100%).

Step 5: A solution of the above dimeric diester (277 mg, 0.51 mmol) in LiOH (10 mL, 1.0 M) and THF (10 mL) was stirred at room temperature for 18 hours. The crude reaction mixture was then diluted with ether (75 mL) and the phases separated. The aqueous layer was acidified to pH 2 with 2.0 M aqueous HCl solution and then extracted with ethyl acetate (4×50 mL). The organic fractions were combined, dried (MgSO$_4$), filtered and concentrated to give 4,4'-bis-2-methoxy-3-{[(m-carboxy)phenoxy]methyl}-pyridine as a colorless solid. This material was used in the next step without further purification. MS (APCI) m/z 517 (M$^+$+1, 100%), 515 (M$^+$–1, 100%).

Step 6: Hydrolysis of the above methoxy-pyridine gave 4,4'-bis-{3-[(m-carboxyphenoxy)methyl]-2-pyridone}.

Experiment 24

This experiment illustrates Fc receptor modulating activity of a tripeptide and a hexapeptide.

Peptide Production

Solid phase peptide synthesis (SPPS) was used to produce an acetylated tripeptide of sequence GKS and hexapeptide of sequence FQNGKS. See for example, Merrifield, *J. Am. Chem. Soc.*, 1963, 85, 2419, and Merrifield et al., *Anal. Chem.*, 1966, 38, 1905. The peptides were synthesized on a 432A synergy Peptide Synthesizer. Construction of peptides was based on Fmoc chemistry (Carpino et al., *J. Org. Chem.* 1972, 37, 3404), while amidated C-terminal resins were used as starting material. Once construction of peptides was complete, an active ester was generated to react with peptide and produce an acetylated N-terminus.

Standard TFA cleavage procedures (Fmoc compatible) were performed and the product were purified using reversed-phase high-performance liquid chromatography (RP-HPLC). (See for example, Mant, C. T. and Hodges, R. S. eds, 1991, "High-Performance Liquid Chromatography of Peptides and Proteins: Separation, Analysis and Confirmation," CRC Press, Boca Raton, Fla.). The two mobile phases were, 0.1% trifluoroacetic acid (TFA)/99% $H_2O$ and 0.1% TFA/60% $CH_3CN$/39.9% $H_2O$. The stationary phase was a prep grade C8 Brownlee Column. Mass spectral analysis was obtained on the final product, which confirmed identity and a purity of greater than 95% for both peptides.

Analysis of FcγRIIa Binding in the Presence of Hexa or Tripeptides

Analysis of the interaction between the baculovirus derived FcγRIIa and peptide (tripeptide: GKS, hexapeptide: FQNGKS) was performed using a BIAcore 2000 biosensor (Pharmacia Biotech, Uppsala, Sweden) at 22° C. in Hepes buffered saline (HBS: 10 mM Hepes, (pH 7.4), 150 mM NaCl, 3.4 mM EDTA, 0.005% Surfactant P20 (Pharmacia). Monomeric human IgG1, IgG3, and IgE (50 μg/mL), were covalently coupled to the carboxymethylated dextran surface of the CM-5 sensor-chip (BIAcore, Uppsala, Sweden) using the amine coupling protocol (BIAcore, Uppsala, Sweden). A channel with no Ig attached was also chemically treated using the coupling protocol. FcγRIIa at a fixed concentration (50 μg/mL, 50% binding concentration) was mixed with a range of peptide concentrations (see FIGS. 10 and 11), for 1 hour at 22° C. before the mixture was injected over the sensor-chip surface for 1 min at 20 μL/min followed by a 3 minute dissociation phase. At the conclusion of the concentration dependence measurements all surfaces were regenerated using 50 mM diethylamine (pH 11.5), 1 M NaCl. The total response measured for each concentration of peptide was determined and plotted against the peptide concentration. The non-specific binding responses (IgE channel) were subtracted from binding to IgG1 or IgG3.

Results

Figure 10:
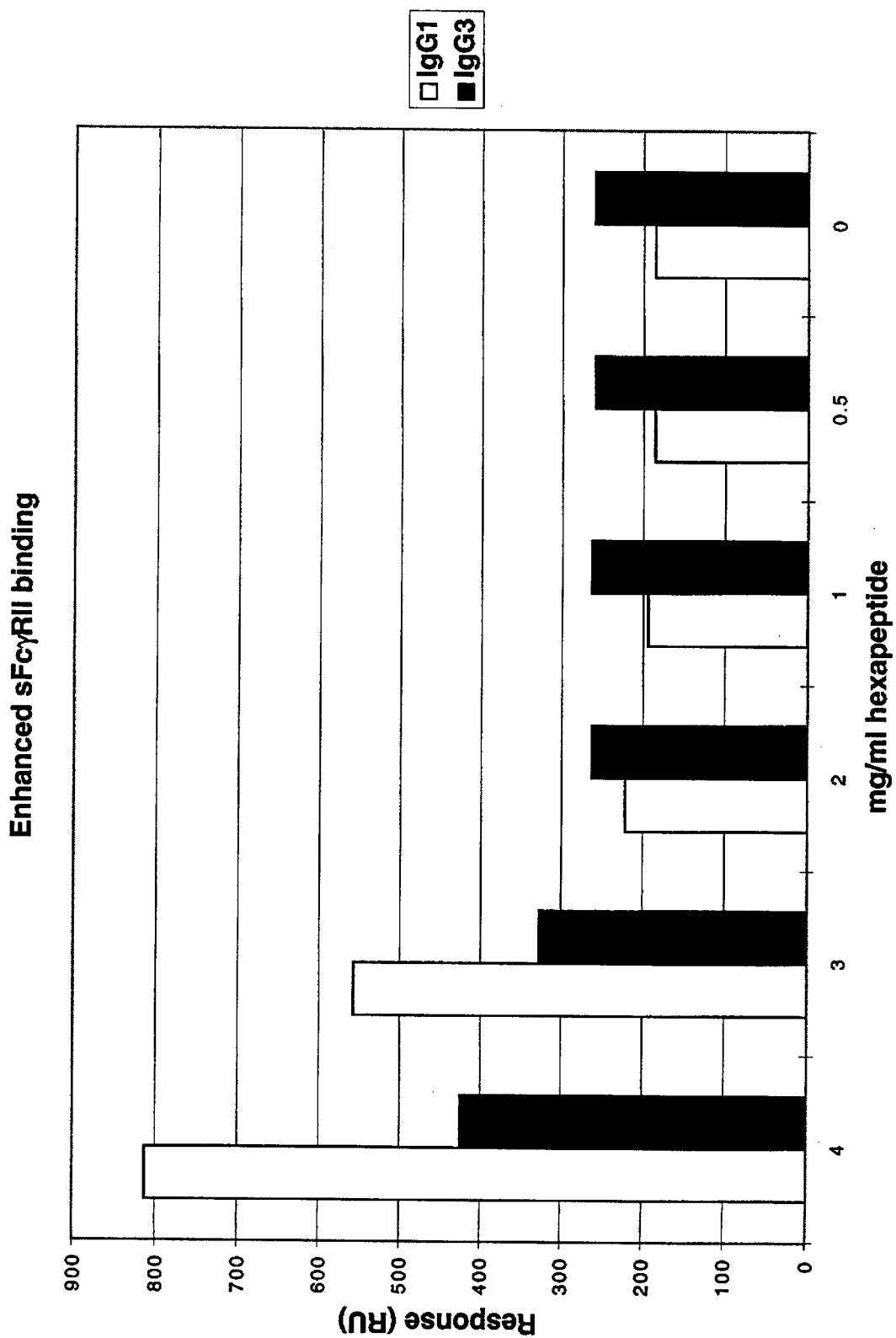
FIG. 10 shows enhanced sFcγRII binding of IgG1 and IgG3 in the presence of a hexapeptide.
Figure 11:
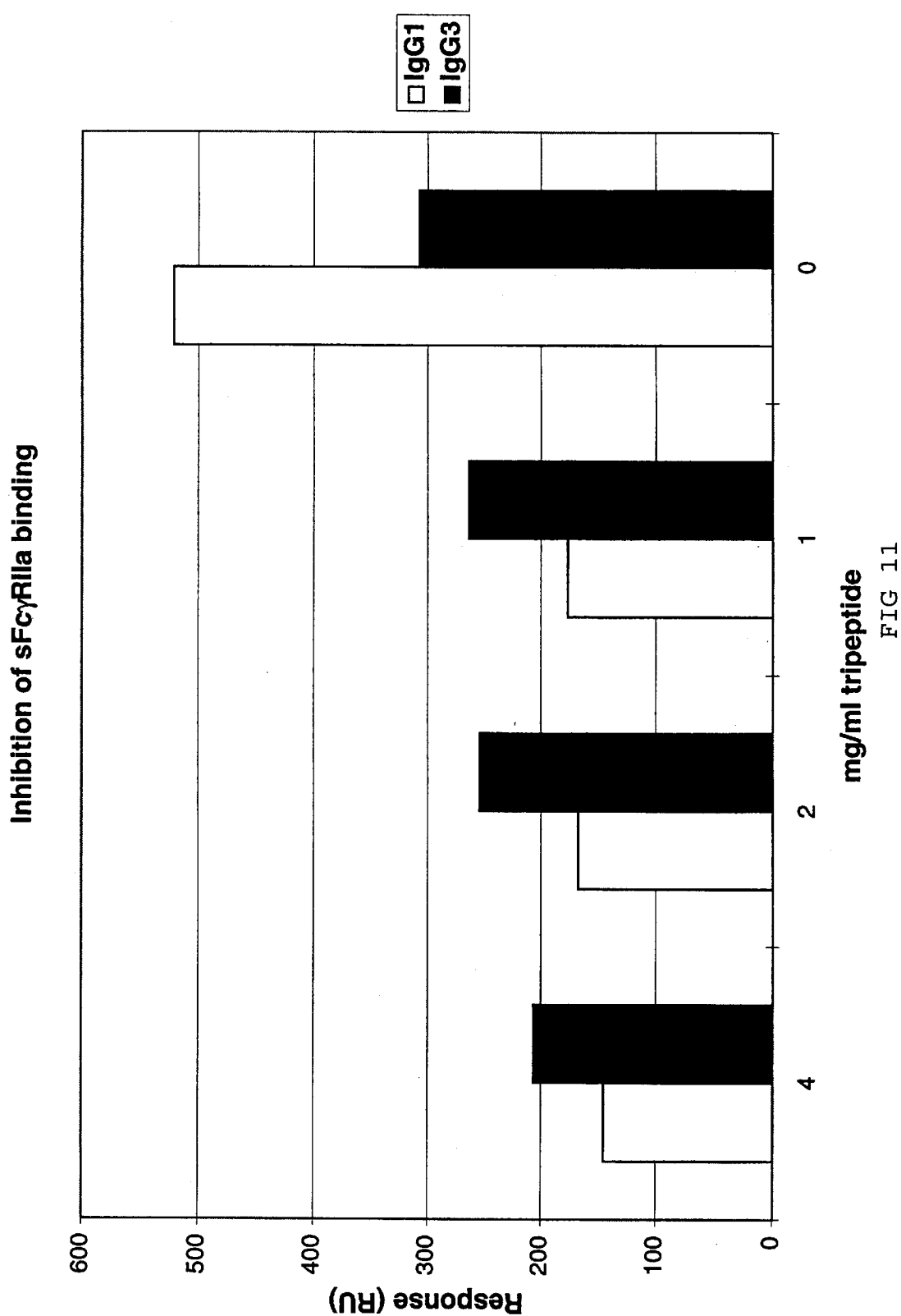
FIG. 11 shows inhibition of sFcγRII binding to IgG1 and IgG3 in the presence of a tripeptide.

Using the sensitivity of surface plasmon resonance (SPR), the binding of soluble FcγRIIa to IgG1 and IgG3 was examined in the presence of a hexapeptide (FQNGKS) or tripeptide (GKS). In the presence of the hexapeptide, the binding of soluble FcγRIIa to the immobilized IgG1 was enhanced four fold and 1.6 fold for interaction with IgG3 (FIG. 10). However, the interaction of soluble FcγRIIa with IgG1 or IgG3 in the presence of the tripeptide was inhibited over a similar peptide concentration range (0–4 mg/mL, FIG. 11).

Experiment 25

This experiment illustrates platelet aggregation inhibition activity of some of the compounds of the present invention. The procedure generally involves adding the compound to a mixture of the platelets and HAGG. Without being bound by any theory, it is believed that this procedure shows the ability of the compound to inhibit a platelet aggregate formation as well as its ability to break apart the platelet aggregates which have formed prior to the addition of the compound.

Platelets express a single class of gamma receptors, FcγRIIa. Following the cross-linking of FcγRIIa, platelets undergo a variety of biochemical and cellular modifications that culminate in aggregation. The capacity of the compounds to inhibit platelet activation was measured using an assay that specifically measures platelet aggregation.

Material and Method

Platelets were isolated as follows: 30 mL of fresh whole blood was collected into citrated collection vials and centrifuged at 1000 rpm for ten minutes. The platelet rich plasma was separated and centrifuged at 2000 rpm for five minutes in four tubes. The supernatants were removed and the platelets were gently resuspended in 2 mL of Tyrodes buffer per tube (137 mM NaCl, 2.7 mM KCl, 0.36 mM $NaH_2PO_4$, 0.1% dextrose, 30 mM sodium citrate, 1.0 mM $MgCl_2.6H_2O$, pH 6.5) and centrifuged again at 2000 rpm for five minutes. The supernatants were again removed and platelets were resuspensed in 0.5 mL of Hepes containing Tyrodes buffer per tube (137 mM NaCl, 2.7 mM KCl, 0.36 mM $NaH_2PO_4$, 0.1% dextrose, 5 mM Hepes, 2 mM $CaCl_2$ 1.0 mM $MgCl_2.6H_2O$, pH 7.35). The platelet count was determined using a haematolog analyzer (Coulter) and adjusted to a concentration of approximately $100 \times 10^5$ platelets/mL using the Hepes containing Tyrodes buffer.

For each aggregation experiment, a mixture of 50 μL of the Fc receptor agonist, heat aggregated gamma globulin ("HAGG", 200 μg/mL) or collagen (2 μg/mL) was incubated with 50 μL of phosphate buffered saline ("PBS": 3.5 mM $NaH_2PO_4$, 150 mM NaCl) or BRI compound (5 mg/mL in PBS) for 60 minutes at room temperature. The assay was then performed using a two cell aggregometer at 37° C. as follows: glass cuvettes were placed in holders and pre-warmed to 37° C. and 400 μL of the platelet suspension added. After a stable baseline was reached, 100 μL of HAGG:PBS, HAGG:BRI compound or collagen:PBS, collagen:BRI compound were added to the platelet suspension. The subsequent aggregation of the platelets was monitored for 15 minutes or until aggregation was complete. The rate of aggregation as determined by measuring the gradient of the aggregation slope.

Results

Figure 12:
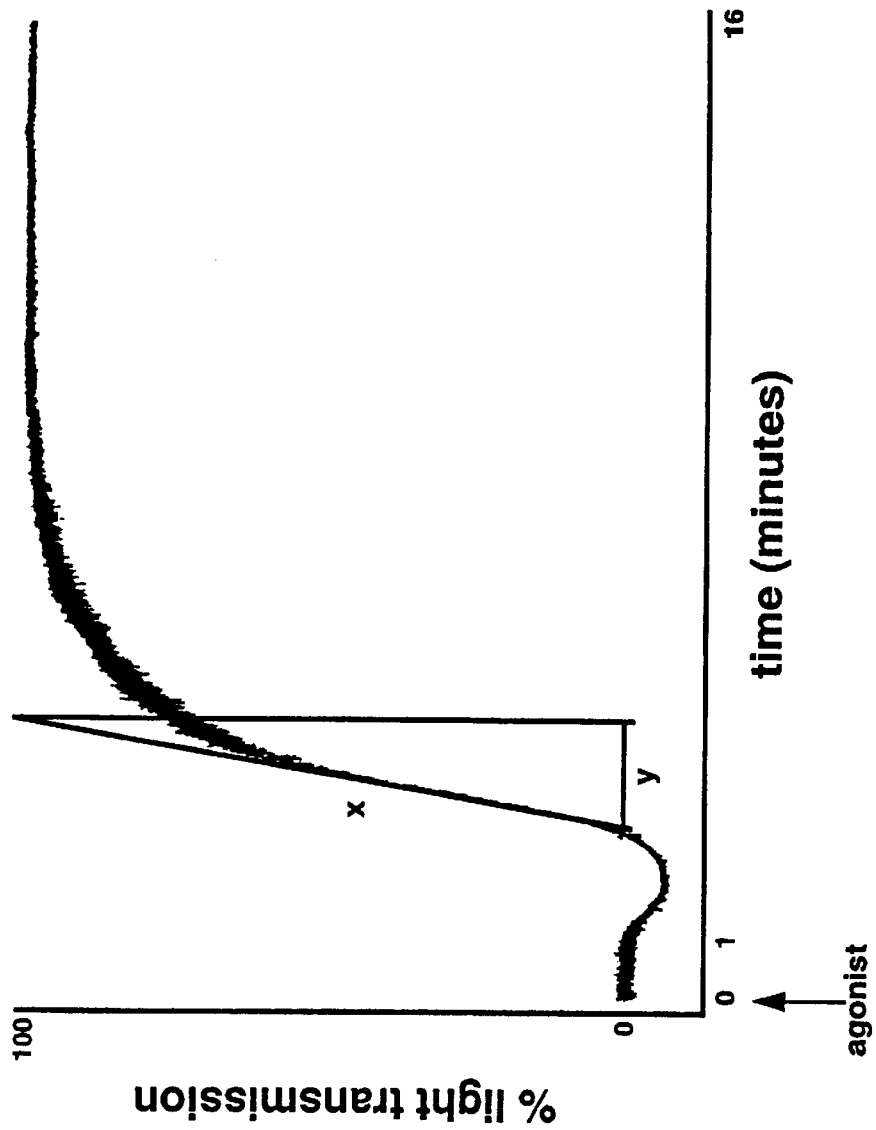
FIG. 12 is a plot of increased light transmission over time in the presence of agonist only.
Figure 13:
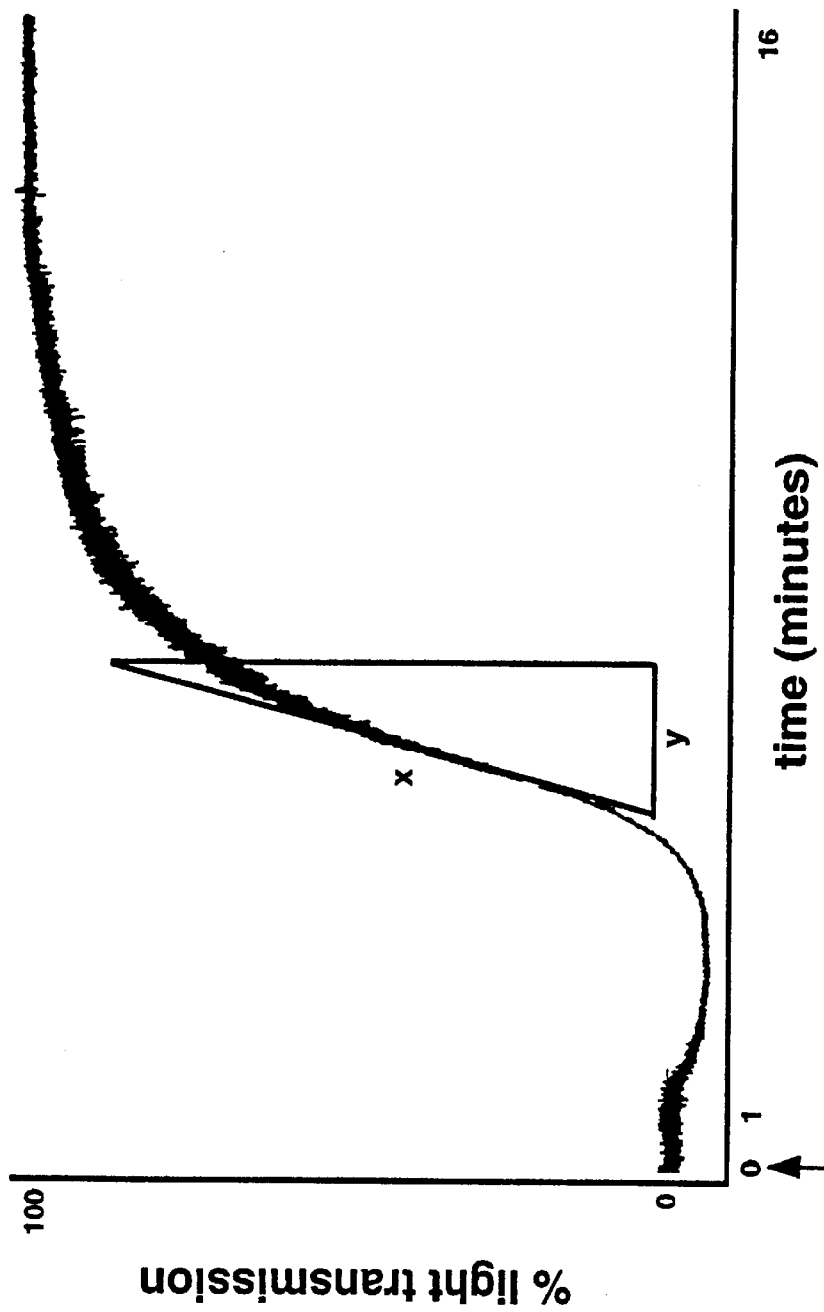
FIG. 13 is a plot of increased light transmission over time in the presence of agonist and BRI6855 compound.

The ability of compounds (BRI6855, BRI6803, BRI6813, BRI6864, BRI6856, BRI6868, BRI7002) to inhibit the HAGG induced FcγRIIa dependent aggregation was examined. The rate of platelet aggregation, measured as the ratio of increased light transmission (y) over time (x), see for example, FIGS. 12 and 13, in the presence of compounds BRI6855, BRI6803, BRI6813, BRI6864 and BRI6856 was reduced compared to the rate achieved when using the FcγRIIa agonist, heat aggregated gamma globulin (100%), see Table 1. Compounds BRI6868 and BRI7002 did not appear to significantly inhibit the rate of platelet activation, Table 1. Compounds BRI6855 and BRI6803 reduced HAGG induced platelet aggregation but did not significantly inhibit the collagen induced platelet aggregation. This indicates activities of BRI6855 and BRI6803 are specific for HAGG.

TABLE 1

Rate of platelet activation in the presence of FcγRIIa agonists or antagonists

| | Rate of platelet aggregation (%) | |
|---|---|---|
| Compound | Expt. 1 | Expt. 2 |
| HAGG + PBS | 100 | 100 |
| HAGG + BRI6855 | 56 | 57 |
| HAGG + BRI6803 | 56 | 58 |
| HAGG + BRI6813 | 82 | 93 |
| HAGG + BRI6864 | 63 | NT |
| HAGG + BRI6856 | 82 | 50 |
| HAGG + BRI6868 | 113 | 116 |
| HAGG + BRI7002 | 92 | NT |

TABLE 1-continued

Rate of platelet activation in the presence of FcγRIIa agonists or antagonists

| Compound | Rate of platelet aggregation (%) | |
|---|---|---|
| | Expt. 1 | Expt. 2 |
| Collagen + PBS | 100 | 100 |
| Collagen + BRI6855 | 100 | NT |
| Collagen + BRI6803 | 73 | NT |

100% is the value of the slope obtained for platelet aggregation using HAGG.
Note that in every experiment effect of compound was simultaneously compared to HAGG induced aggregation.
NT = Not Tested.

Experiment 26

This experiment illustrates platelet aggregation inhibition activity of some of the compounds of the present invention. The procedure generally involves adding HAGG to a mixture of the platelets and the compound. Without being bound by any theory, it is believed that unlike Experiment 25, this method only shows the ability of the compound to inhibit the formation of platelet aggregates.

Material and Method

Experimental procedure of Experiment 25 was used to isolate platelets and determine the platelet count.

Unlike Experiment 25, the platelet aggregation assay was performed by adding 50 mL of PBS or BRI compound to the platelet suspension. After about one minute, 50 mL of agonist (HAGG, collagen ADP) was added to the platelet suspension. The subsequent aggregation of the platelets was monitored for 10–15 minutes or until aggregation was complete. The rate of aggregation was determined by measuring the gradient of the aggregation slope.

Results

Figure 14:
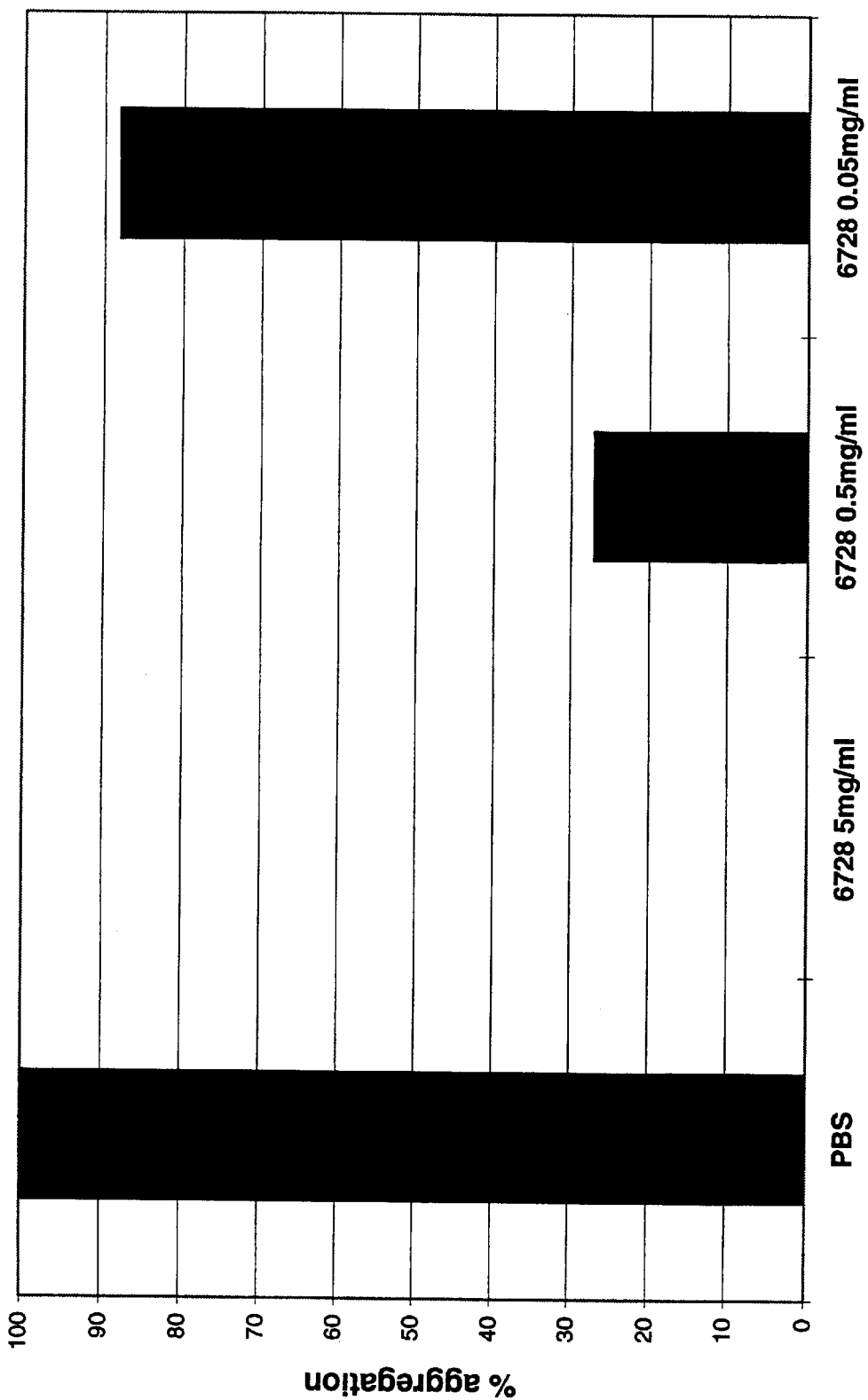
FIG. 14 is a plot of % platelet aggregation at a various concentrations of BRI6728 compound.

The ability of compound BRI6728 to inhibit the HAGG induced FcgRIIa dependent aggregation was examined. The rate of platelet aggregation, measured as the ratio of increased light transmission (y) over time (x), see for example, FIG. 14, in the presence of titrating amounts of the compound BRI6728 was reduced compared to the rate achieved when using the FcgRIIa agonist, heat aggregated gamma globulin (100%), see FIG. 14. Results of platelet aggregation using other compounds are shown on Table 2.

TABLE 2

Platelet aggregation in the presence of a various compounds.

| Compound | Amount of platelet aggregation | |
|---|---|---|
| | Expt. 1 | Expt. 2 |
| PBS | 100 | NT |
| BRI6855 | 81 | NT |
| BRI6864 | 41 | NT |
| BRI6829 | 35 | NT |
| BRI6816 | 0 | 0 |
| BRI6734 | 0 | NT |
| BRI6727 | 0 | NT |
| BRI6728 | 0 | 0 |
| BRI6822 | 0 | 0 |
| BRI6817 | 75 | NT |

100% is the amount of platelet aggregation obtained using PBS. NT=Not Tested.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A pharmaceutical composition comprising:

(a) compound having the formula:

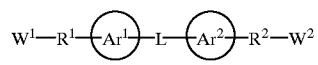

or salts thereof, wherein
each of $W^1$ and $W^2$ is independently $CO_2R^3$ having a PKa between about 7 and about 3.75;
each of $Ar^1$ and $Ar^2$ is independently phenyl or napthyl;
each of $R^1$ and $R^2$ is a bond, $CH_2$, or $C_2$–$C_6$ alkylene;
$R^3$ is independently hydrogen or $C_1$–$C_6$ alkyl; and
L is a linker comprising from 1 to about 10 atoms selected from the group consisting of alkyl, alkylene, ketone, alkenone, alcohol and diol; and (b) a pharmaceutically acceptable carrier.

2. The composition of claim 1, wherein said compound is of the formula:

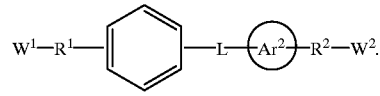

3. The composition of claim 2, wherein said compound is of the formula:

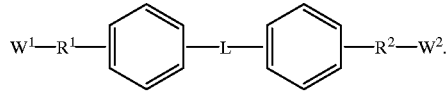

4. The composition of claim 3, wherein $W^1$ and $W^2$ are $CO_2H$.

5. The composition of claim 4, wherein $R^1$ and $R^2$ are a bond.

6. The composition of claim 5, wherein $L^1$ is —$CH_2CH_2$—.

7. The composition of claim 5, wherein $L^1$ is —CH=CHC(=O)—.

8. The composition of claim 5, wherein $L^1$ is —$CH_2CH_2CH(OH)$—.

9. The composition of claim 5, wherein $L^1$ is —CH=CH—.

10. The composition of claim 5, wherein $L^1$ is —CH(OH)CH(OH)—.

11. The composition of claim 10, wherein the stereochemistry of hydroxy groups is (S,S).

12. The composition of claim 4, wherein $R^1$ and $R^2$ are —$CH_2$—.

13. The composition of claim 12, wherein $L^1$ is ethylene.

14. The composition of claim 12, wherein $L^1$ is —CH=CH—.

15. The composition of claim 4, wherein $R^1$ is methylene, $R^2$ is a bond and $L^1$ is ethylene.

16. The composition of claim 1, wherein the compound is of the formula:

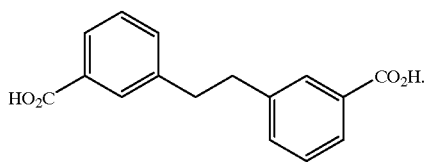

17. The composition of claim 1, wherein the compound is of the formula:

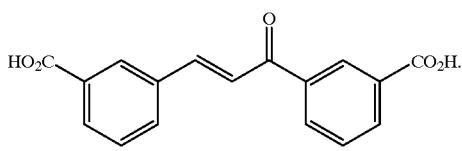

18. The composition of claim 1, wherein the compound is of the formula:

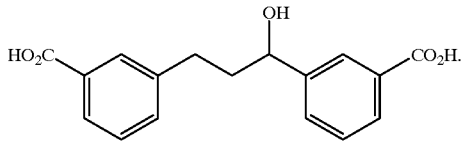

19. The composition of claim 1, wherein the compound is of the formula:

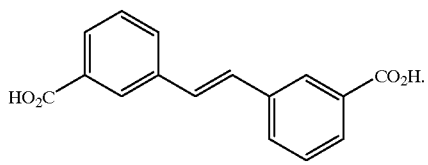

20. The composition of claim 1, wherein the compound is of the formula:

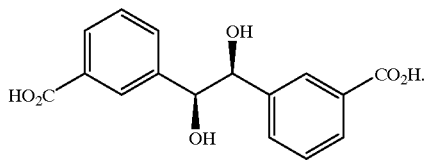

21. The composition of claim 1, wherein the compound is of the formula:

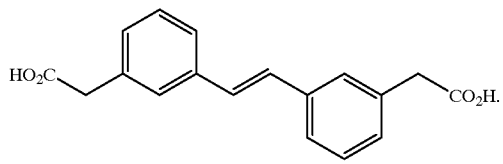

22. The composition of claim 1, wherein the compound is of the formula:

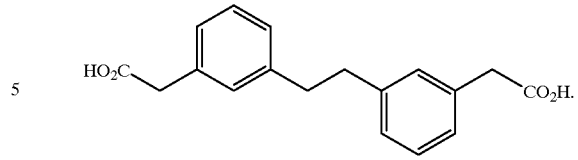

23. The composition of claim 1, wherein the compound is of the formula:

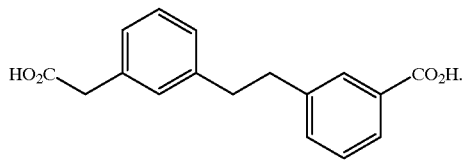

24. A method for inhibiting Fc receptor binding of immunoglobulin in a patient comprising administering to such patient a pharmaceutically effective amount of a compound of the formula:

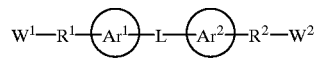

or salts thereof,
wherein
each of $W^1$ and $W^2$ is independently $CO_2R^3$ having a pKa of between about 7 and about 3.75,
each of $Ar^1$ and $Ar^2$ is independently phenyl or napthyl;
each of $R^1$ and $R^2$ is a bond, $CH_2$, or $C_2$–$C_6$ alkylene;
$R^3$ is independently hydrogen or $C_1$–$C_6$ alkyl; and
L is a linker comprising from 1 to about 10 atoms selected from the group consisting of allyl, alkylene, ketone, alkenone, alcohol and diol.

25. The method of claim 24, wherein said Fc receptor is selected from the group consisting of FcαR, FcεR, FcγR and mixtures thereof.

26. The method of claim 25, wherein said Fc receptor is selected from the group consisting of FcγRIIa, FcγRIIb, FcγRIIc and mixtures thereof.

27. The method of claim 24, wherein said method reduces IgG-mediated tissue damage in said patient.

28. The method of claim 24, wherein said method reduces inflammation in said patient.

29. The method of claim 24, wherein said method is used to treat an autoimmune disease.

30. The method of claim 24, wherein said method is used to treat a disease where aggregates of antibodies are produced or where immune complexes are produced by contact of antibody with intrinsic or extrinsic antigen.

31. The method of claim 30, wherein said disease is selected from the group consisting of immune complex diseases, autoimmune diseases, infectious diseases and vasculitities.

32. The method of claim 31, wherein said autoimmune disease is selected from the group consisting of rheumatoid arthritis, systemic lupus erythematosus, immune thrombocytopenia, neutropenia, and hemolytic anaemias.

33. The method of claim 31, wherein said vasculitities is selected from the group consisting of polyarteritis nodosa, and systemic vasculitis.

34. The method of claim 31, wherein said infectious disease is selected from the group consisting of Dengue virus-dengue hemorrhagic fever and measles virus infection.

35. The method of claim 24, wherein said method is used to treat xenograft rejection.

36. The method of claim 24, wherein said method reduces IgE-mediated response in said patient.

37. The method of claim 24, wherein said compound is of the formula:

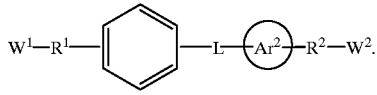

38. The method of claim 37, wherein said compound is of the formula:

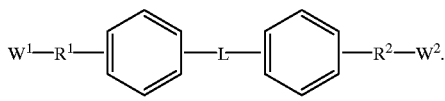

39. The method of claim 38, wherein $W^1$ and $W^2$ are $CO_2H$.

40. The method of claim 39, wherein $R^1$ and $R^2$ are a bond.

41. The method of claim 40, wherein $L^1$ is —$CH_2CH_2$—.

42. The method of claim 40, wherein $L^1$ is —CH=CHC(=O)—.

43. The method of claim 40, wherein $L^1$ is —$CH_2CH_2$CH(OH)—.

44. The method of claim 40, wherein $L^1$ is —CH=CH—.

45. The method of claim 40, wherein $L^1$ is —CH(OH)CH(OH)—.

46. The method of claim 45, wherein the stereochemistry of hydroxy groups is (S,S).

47. The method of claim 39, wherein $R^1$ and $R^2$ are —$CH_2$—.

48. The method of claim 47, wherein $L^1$ is ethylene.

49. The method of claim 47, wherein $L^1$ is —CH=CH—.

50. The method of claim 39, wherein $R^1$ is methylene, $R^2$ is a bond and $L^1$ is ethylene.

* * * * *